(12) United States Patent  (10) Patent No.: US 9,120,793 B2
Hamdouchi  (45) Date of Patent: Sep. 1, 2015

(54) TRIAZOLO-PYRIDINE COMPOUND

(71) Applicant: Eli Lilly and Company, Indianapolis, IN (US)

(72) Inventor: Chafiq Hamdouchi, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/559,956

(22) Filed: Dec. 4, 2014

(65) Prior Publication Data

US 2015/0166535 A1  Jun. 18, 2015

Related U.S. Application Data

(60) Provisional application No. 61/915,774, filed on Dec. 13, 2013.

(51) Int. Cl.
C07D 401/14 (2006.01)
A61K 31/437 (2006.01)
C07D 471/04 (2006.01)

(52) U.S. Cl.
CPC .................. C07D 471/04 (2013.01)

(58) Field of Classification Search
CPC .............. C07D 401/14; A61K 31/437
USPC .......................... 546/119; 514/303
See application file for complete search history.

(56) References Cited

U.S. PATENT DOCUMENTS 7,820,837 B2  10/2010  Yasuma et al.
7,960,369 B2  6/2011  Kukatsu et al.

FOREIGN PATENT DOCUMENTS

EP  1559422  6/2003
WO  2005086661  9/2005
WO  2014073904  5/2014

OTHER PUBLICATIONS

Potts et al., Journal of Organic Chemistry (1966), 31(1), 260-5.*

* cited by examiner

*Primary Examiner* — Niloofar Rahmani
(74) *Attorney, Agent, or Firm* — MaCharri Vorndran-Jones

(57) ABSTRACT

The present invention provides compounds of the formula

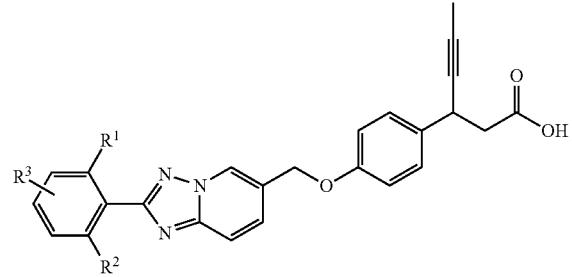

wherein
$R^1$ is selected from the group consisting of H and $CH_3$;
$R^2$ is selected from the group consisting of H and $CH_3$;
$R^3$ is selected from the group consisting of H, $C_1$-$C_3$ alkyl, $O(CH_2)_3SO_2CH_3$, $O(CH_2)_2OCH_3$, $O(CH_2)_2C(CH_3)_2OH$, CN, and $OCF_2$;
or a pharmaceutical salt thereof, methods of treating diabetes, intermediates, and a process for preparing compounds of the invention.

16 Claims, 2 Drawing Sheets

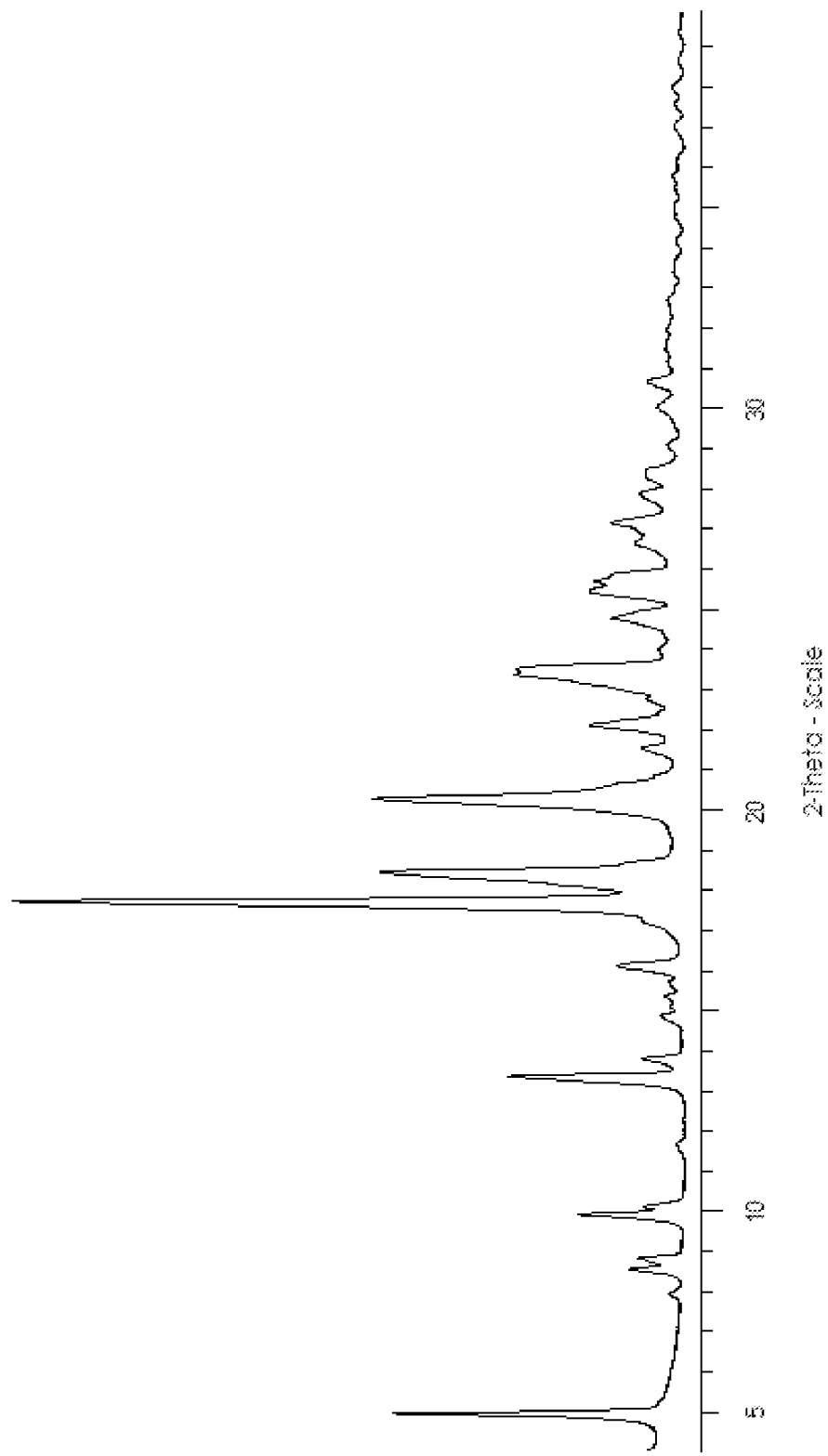

TRIAZOLO-PYRIDINE COMPOUND

Figure 1:
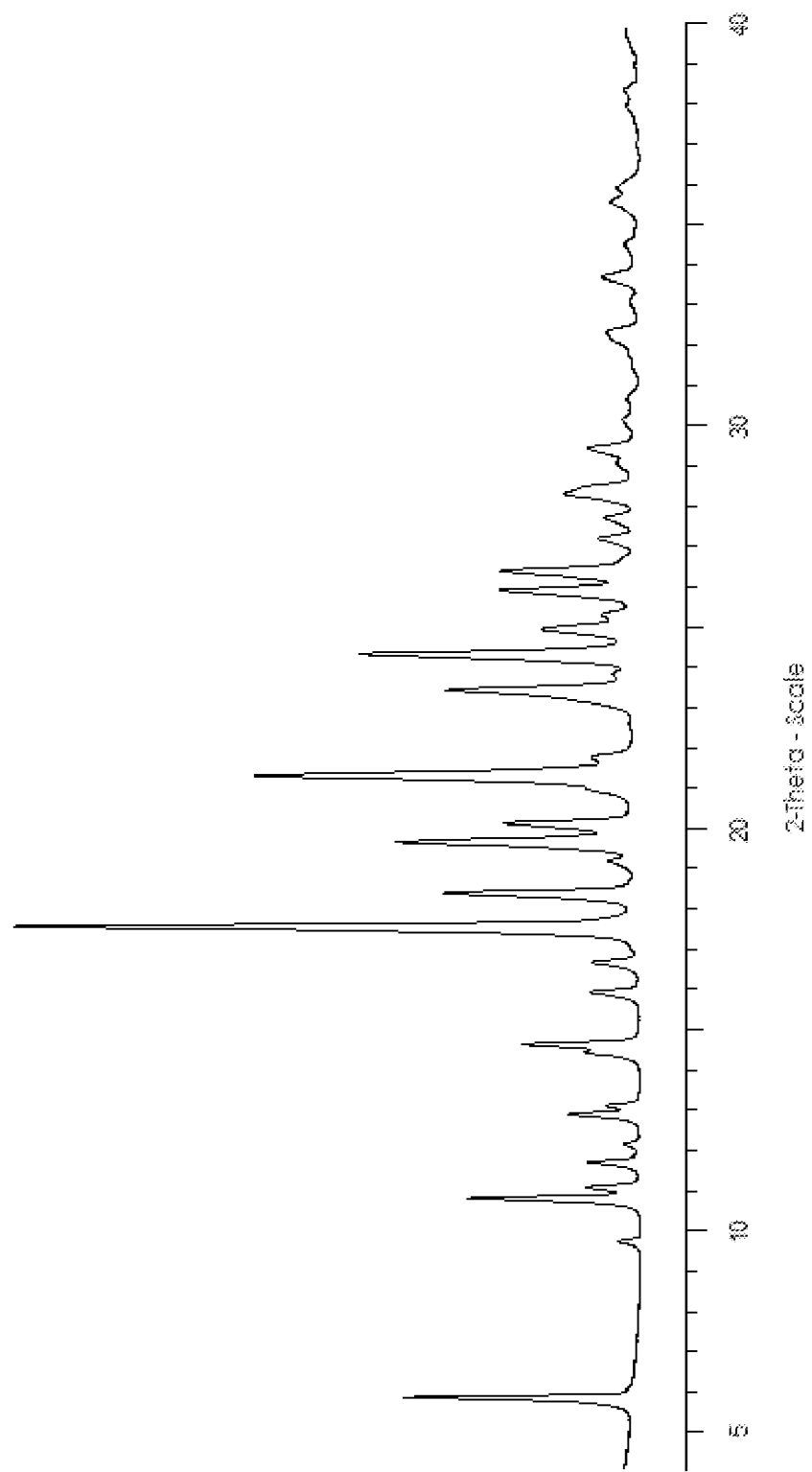

This invention relates to triazolo-pyridine compounds or pharmaceutically acceptable salts thereof, and for use of compounds in therapy. Triazolo-pyridine compounds of this invention are activators of GPR-40.

GPR-40, also known as Free Fatty Acid Receptor 1 (FFA1 or FFAR1), is reported as predominately expressed at high levels in rodent pancreatic beta cells, insulinoma cell lines, and human islets. The glucose modulation of insulin secretion is an important feature of activating GPR-40. Compounds that effectuate GPR-40 activation are associated with stimulation of insulin secretion in a patient with type II diabetes (T2D). Compounds that are GPR-40 activators are desired for use in treatment of GPR-40 mediated conditions.

WO2004/041266 discloses GPR-40 receptor function regulators comprising a compound having an aromatic ring and a group capable of releasing a cation.

In a brief description of the drawings, FIG. 1 is a spectrogram of representative XRD pattern for (3S)-3-[4-[[2-(2,6-Dimethylphenyl)-[1,2,4]triazolo[1,5-a]pyridin-6-yl]methoxy]phenyl]hex-4-ynoic acid, Form II. FIG. 2 is a spectrogram of representative XRD pattern for (3S)-3-[4-[[2-(2,6-Dimethylphenyl)-[1,2,4]triazolo[1,5-a]pyridin-6-yl]methoxy]phenyl]hex-4-ynoic acid, Form I.

The present invention provides compounds of the Formula Ia below:

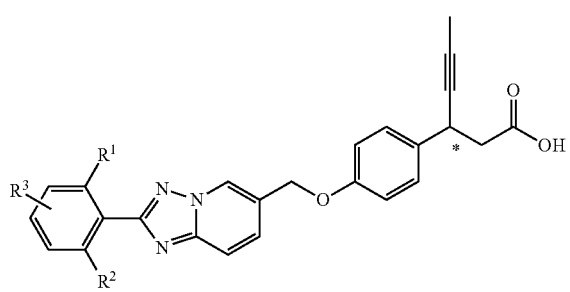

Ia wherein

R$^1$ is selected from the group consisting of H and CH$_3$;

R$^2$ is selected from the group consisting of H and CH$_3$;

R$^3$ is selected from the group consisting of H, C$_1$-C$_3$ alkyl, O(CH$_2$)$_3$SO$_2$CH$_3$, O(CH$_2$)$_2$OCH$_3$, O(CH$_2$)$_2$C(CH$_3$)$_2$OH, CN, and OCF$_2$;

or a pharmaceutically acceptable salt thereof.

A compound of the present invention has a chiral carbon identified in the structure above with an asterisk (*). A preferred compound has the configuration shown in Formula I, below, which by convention is known as the S configuration. The present invention provides compounds of the Formula Ib below:

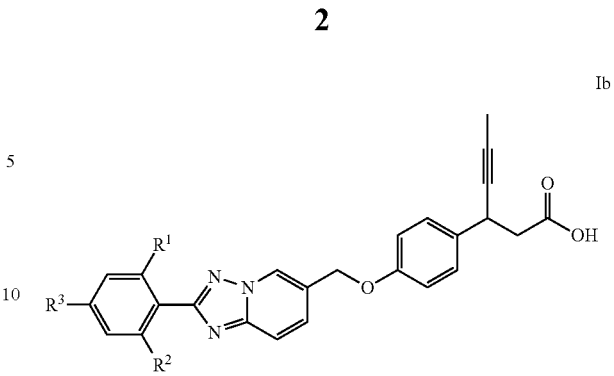

Ib wherein

R$^1$ is selected from the group consisting of H and CH$_3$;

R$^2$ is selected from the group consisting of H and CH$_3$;

R$^3$ is selected from the group consisting of H, C$_1$-C$_3$ alkyl, O(CH$_2$)$_3$SO$_2$CH$_3$, O(CH$_2$)$_2$OCH$_3$, O(CH$_2$)$_2$C(CH$_3$)$_2$OH, CN, and OCF$_2$;

or a pharmaceutically acceptable salt thereof.

The present invention provides a compound of the Formula I below:

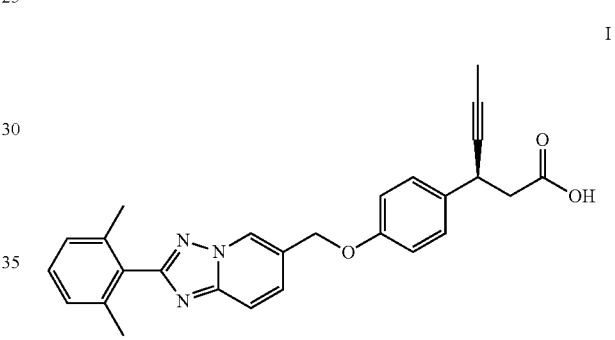

I or a pharmaceutically acceptable salt thereof.

In an embodiment, the compound of Formula I is the anhydrous crystalline Form I.

In an embodiment, the compound of Formula I is the anhydrous crystalline Form II.

In an embodiment R$^1$ is H; R$^2$ is CH$_3$; and R$^3$ is selected from the group consisting of H, C$_1$-C$_3$ alkyl, and CN. In another embodiment R$^1$ is H; R$^2$ is H; and R$^3$ is H. In another embodiment R$^1$ is H; R$^2$ is H; and R$^3$ is selected from the group consisting of O(CH$_2$)$_3$SO$_2$CH$_3$, O(CH$_2$)$_2$OCH$_3$, O(CH$_2$)$_2$C(CH$_3$)$_2$OH, CN, and OCF$_2$. In another embodiment R$^1$ is CH$_3$; R$^2$ is CH$_3$; and R$^3$ is C$_3$ alkyl. R$^1$ is H; R$^2$ is H; and R$^3$ is O(CH$_2$)$_3$SO$_2$CH$_3$. In another embodiment R$^1$ is CH$_3$; R$^2$ is CH$_3$; and R$^3$ is H. In another embodiment R$^1$ is H; R$^2$ is CH$_3$; and R$^3$ is selected from the group consisting of O(CH$_2$)$_3$SO$_2$CH$_3$, O(CH$_2$)$_2$OCH$_3$, and O(CH$_2$)$_2$C(CH$_3$)$_2$OH.

The present invention also provides a pharmaceutical composition comprising a compound of Formula I as described above or a pharmaceutically acceptable salt thereof together with one or more pharmaceutically acceptable carriers, diluents or excipients.

The present invention also provides a pharmaceutical composition comprising a compound of Formula I as described above or a pharmaceutically acceptable salt thereof together with one or more pharmaceutically acceptable carriers, diluents or excipients, and optionally in combination with one or more therapeutic agents. Additional therapeutic agents include for example, metformin and/or Januvia. In an embodiment of the invention the additional therapeutic is metformin In an embodiment of the invention the additional therapeutic agent is Januvia.

The present invention also provides a pharmaceutical composition comprising a compound of Formula Ia as described above or a pharmaceutically acceptable salt thereof together with one or more pharmaceutically acceptable carriers, diluents or excipients.

The present invention also provides a pharmaceutical composition comprising a compound of Formula Ia as described above or a pharmaceutically acceptable slat thereof together with one or more pharmaceutically acceptable carriers, diluents or excipients, and optionally in combination with one or more therapeutic agents. Additional therapeutic agents include for example, metformin and/or Januvia. In an embodiment of the invention the additional therapeutic is metformin In an embodiment of the invention the additional therapeutic agent is Januvia.

The present invention provides a method for treating a condition modulated by GPR-40 activity. The present invention also provides a method for treating diabetes in a mammal. The method comprises administering to the mammal in need of treatment, an effective amount of a compound of Formula I, or a pharmaceutically acceptable salt thereof. The method comprises administering to the mammal in need of treatment an effective amount of a compound of Formula Ia, or a pharmaceutically acceptable salt thereof. More preferably the present invention provides a method of treating type two diabetes in a mammal in need of treatment comprising administering to the mammal an effective amount of a compound of Formula I or a pharmaceutically acceptable salt thereof.

More preferably the present invention provides a method of treating type two diabetes in a mammal in need of treatment comprising administering to the mammal an effective amount of a compound of Formula Ia or a pharmaceutically acceptable salt thereof. Preferably the mammal is a human.

The present invention provides a compound according to Formula I or a pharmaceutically acceptable salt thereof as described above for use in therapy.

The present invention provides a compound according to Formula Ia or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of diabetes. In yet another form, the present invention provides a compound as described above according to Formula Ia, a pharmaceutically acceptable salt thereof, or pharmaceutical composition for use in the treatment of diabetes. In another embodiment, a compound as described above according to Formula I, or a pharmaceutically acceptable salt thereof, is for the treatment of type two diabetes. In another embodiment, the pharmaceutical composition is for the treatment of type two diabetes.

The present invention provides use of a compound according to Formula I, or a pharmaceutically acceptable salt thereof, in the manufacture of a medicament for the treatment of diabetes. Preferably the medicament is for the treatment of type two diabetes.

The present invention provides use of a compound according to Formula Ia, or a pharmaceutically acceptable salt thereof, in the manufacture of a medicament for the treatment of diabetes. Preferably the medicament is for the treatment of type two diabetes.

In yet another form, the present invention provides an intermediate compound of the Formula IIa

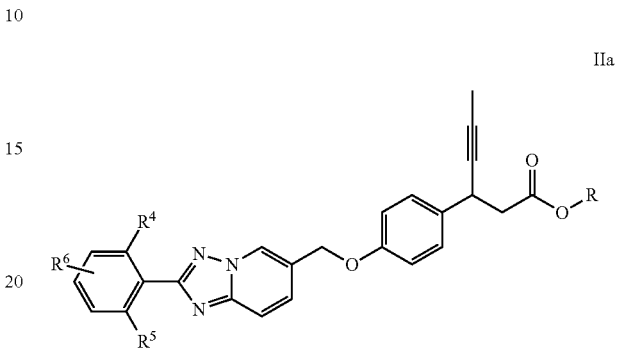

wherein

R is selected from the group consisting of $C_{1-4}$ alkyl, $C_{1-4}$ haloalkyl, $C_{3-6}$ cycloalkyl, —$C_{1-4}$ alkyl-$C_{3-6}$ cycloalkyl, phenyl, and $C_{1-5}$ alkylphenyl;

$R^4$ is selected from the group consisting of H and $CH_3$;

$R^5$ is selected from the group consisting of H and $CH_3$; and $R^6$ is selected from the group consisting of H, $C_1$-$C_3$ alkyl, $O(CH_2)_3SO_2CH_3$, $O(CH_2)_2OCH_3$, $O(CH_2)_2C(CH_3)_2OH$, CN, and $OCF_2$;

or a pharmaceutically acceptable salt thereof.

In yet another form, the present invention provides an intermediate compound of the Formula IIb

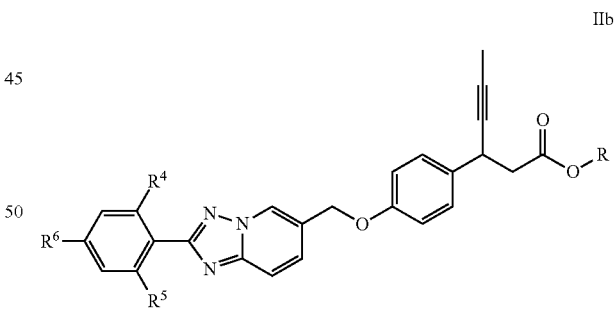

wherein

R is selected from the group consisting of $C_{1-4}$ alkyl, $C_{1-4}$ haloalkyl, $C_{3-6}$ cycloalkyl, —$C_{1-4}$ alkyl-$C_{3-6}$ cycloalkyl, phenyl, and $C_{1-5}$ alkylphenyl;

$R^4$ is selected from the group consisting of H and $CH_3$;

$R^5$ is selected from the group consisting of H and $CH_3$; and $R^6$ is selected from the group consisting of H, $C_1$-$C_3$ alkyl, $O(CH_2)_3SO_2CH_3$, $O(CH_2)_2OCH_3$, $O(CH_2)_2C(CH_3)_2OH$, CN, and $OCF_2$;

or a pharmaceutically acceptable salt thereof.

In yet another form, the present invention provides an intermediate compound of the Formula II

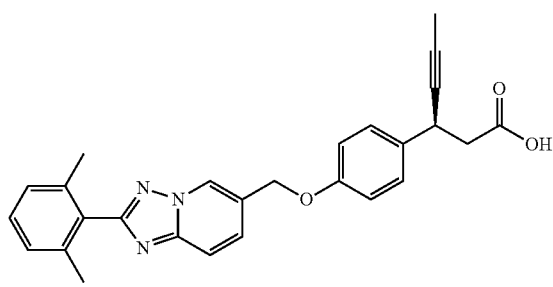

wherein R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl, or a pharmaceutically acceptable salt thereof.

Preferred R groups are selected from the group consisting of $C_{1-4}$ alkyl, $C_{1-2}$ haloalkyl, phenyl, and $C_{1-2}$ alkylphenyl. Particularly preferred R groups are selected from the group consisting of methyl, ethyl, phenyl, and benzyl. Particularly preferred R groups are selected from the group consisting of methyl and ethyl.

In an embodiment R is $C_{1-4}$ alkyl; $R^4$ is H; $R^5$ is $CH_3$; and $R^6$ is selected from the group consisting of H, $C_1$-$C_3$ alkyl, and CN. In an embodiment R is selected from the group consisting of $C_{1-4}$ alkyl, and $C_{1-4}$ haloalkyl; $R^4$ is H; $R^5$ is $CH_3$; and $R^6$ is selected from the group consisting of H, $C_1$-$C_3$ alkyl, and CN. In another embodiment R is selected from the group consisting of $C_{1-4}$ alkyl, $C_{1-4}$ haloalkyl; $R^4$ is H; $R^5$ is H; and $R^6$ is H. In another embodiment R is selected from the group consisting of $C_{1-4}$ alkyl, $C_{1-2}$ haloalkyl, phenyl and $C_{1-2}$ alkylphenyl; $R^4$ is H; $R^5$ is H; and $R^6$ is selected from the group consisting of $O(CH_2)_3SO_2CH_3$, $O(CH_2)_2OCH_3$, $O(CH_2)_2C(CH_3)_2OH$, CN, and $OCF_2$. In another embodiment R is selected from the group consisting of $C_{1-4}$ alkyl, $C_{1-2}$ haloalkyl, phenyl, and $C_{1-2}$ alkylphenyl; $R^4$ is $CH_3$; $R^5$ is $CH_3$; and $R^6$ is $C_3$ alkyl. In another embodiment R is selected from the group consisting of $C_{1-4}$ alkyl; $R^4$ is $CH_3$; $R^5$ is $CH_3$; and $R^6$ is H. In another embodiment R is selected from the group consisting of —$C_{1-4}$ alkyl, $C_{1-2}$ haloalkyl, phenyl, and $C_{1-2}$ alkylphenyl; $R^4$ is H; $R^5$ is $CH_3$; and $R^6$ is selected from the group consisting of $O(CH_2)_3SO_2CH_3$, $O(CH_2)_2OCH_3$, and $O(CH_2)_2C(CH_3)_2OH$.

The present invention also provides a process of preparing (3S)-3-[4-[[2-(2,6-Dimethylphenyl)-[1,2,4]triazolo[1,5-a]pyridin-6-yl]methoxy]phenyl]hex-4-ynoic acid described above for Formula I. The process comprises deprotecting or de-esterifying the intermediate compound according to Formula II to prepare the compound of Formula 1 or a pharmaceutically acceptable salt thereof.

The present invention also provides a process of preparing a compound described above as Formula Ia. The process comprises deprotecting or de-esterifying the intermediate compound according to Formula IIa to prepare the compound of Formula Ia or a pharmaceutically acceptable salt thereof.

One skilled in the art would readily understand and be able to implement deprotecting reactions without undue experimentation. It will be recognized by those skilled in the art that in addition to the carboxylic acid and protected carboxylic acid, other functional groups that can be readily converted to a carboxylic acid can be used in place the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

FIG. 1, (3S)-3-[4-[[2-(2,6-Dimethylphenyl)-[1,2,4]triazolo[1,5-a]pyridin-6-yl]methoxy]phenyl]hex-4-ynoic acid, Form II, and FIG. 2, (3S)-3-[4-[[2-(2,6-Dimethylphenyl)-[1,2,4]triazolo[1,5-a]pyridin-6-yl]methoxy]phenyl]hex-4-ynoic acid, Form I, are spectrograms of representative XRD pattern for (3S)-3-[4-[[2-(2,6-Dimethylphenyl)-[1,2,4]triazolo[1,5-a]pyridin-6-yl]methoxy]phenyl]hex-4-ynoic acid. The XRD spectrograms are obtained as described in Example 1.

The compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "pharmaceutically acceptable carrier, diluent, or excipients" means that the carrier, diluent, and excipients are pharmaceutically compatible with the other ingredients of the composition.

Individual isomers, enantiomers, or diastereomers may be separated at any convenient point in the synthesis of the compound of Formula I or Ia or Ib by methods such as chiral chromatography. Additionally, the intermediates described in the following Schemes and preparations contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The abbreviations used herein are defined according to *Aldrichimica Acta*, Vol. 17, No. 1, 1984. Other abbreviations are defined as follows: "BSA" refers to Bovine Serum Albumin; "DCM" refers to dichloromethane; "DIBAL-H" refers to diisobutylaluminum hydride; "DIPEA" refers to diisopropylethylamine; "DMEM" refers to Dulbecco's Modified Eagle's Medium; "DMF" refers to dimethylformamide; "DTT" refers to dithiothreitol; "$EC_{50}$" refers to the effective concentration at half the maximal response; "EtOAc" refers to ethyl acetate; "EtOH" refers to ethyl alcohol or ethanol; "F12" refers to Ham's F12 medium; "FBS" refers to Fetal Bovine Serum; "HEK" refers to human embryonic kidney; "$IC_{50}$" refers to the concentration of an agent that produces 50% of the maximal inhibitory response possible for that agent; "i.p." refers to intraperitoneal injection; "MCPBA" refers to m-chloroperbenzoic acid; "PPAR" refers to peroxisome proliferator-activated receptor; "PPRE" refers to peroxisome proliferator response element; "PPh3" refers to triphenylphosphate; "RFU" refers to relative fluorescence unit; "THF" refers to tetrahydrofuran; "TK" refers to thymidine kinase; "TAK875" refers to the Takeda compound, (3-[4-(2-methyl-benzyloxy)-phenyl]-hex-4-ynoic acid), known as fasiglifam and "XRD" refers to X-ray powder diffraction.

The term alkyl as used herein is a straight chain alkyl such as ethyl or n-propyl, or a branched chain alkyl such as iso-propyl or tert-butyl. The term $C_{1-4}$ haloalkyl refers to an alkyl group that has 1, 2, 3, or more halo groups attached to the carbons of the alkyl chain. If there are two or more halogens the halogens need not be attached to the same carbon. This term also includes perhalo alkyls where all the hydrogen atoms of the alkyl group are replaced with a halogen.

In the Preparations and Schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow, including any novel procedures.

displaced with bromine using a brominating agent such as $PBr_3$ in a polar aprotic solvent such as DCM at a temperature of about −40° C. to give the product of Step 2. The product of Step 2 can be alkylated with the substituted phenol under common alkylation conditions using an inorganic base such as cesium carbonate or potassium carbonate in a polar aprotic solvent such as DMF or acetonitrile to give the product of Step 3. The halogen product of Step 3 can be coupled in substep 1, Step 4 with an appropriate boronic acid under Suzuki-Miyaura cross coupling conditions. The skilled artisan will recognize that there are a variety of conditions useful for facilitating such cross-coupling reactions. Accordingly, a suitable palladium reagent includes bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. A suit- Scheme 1

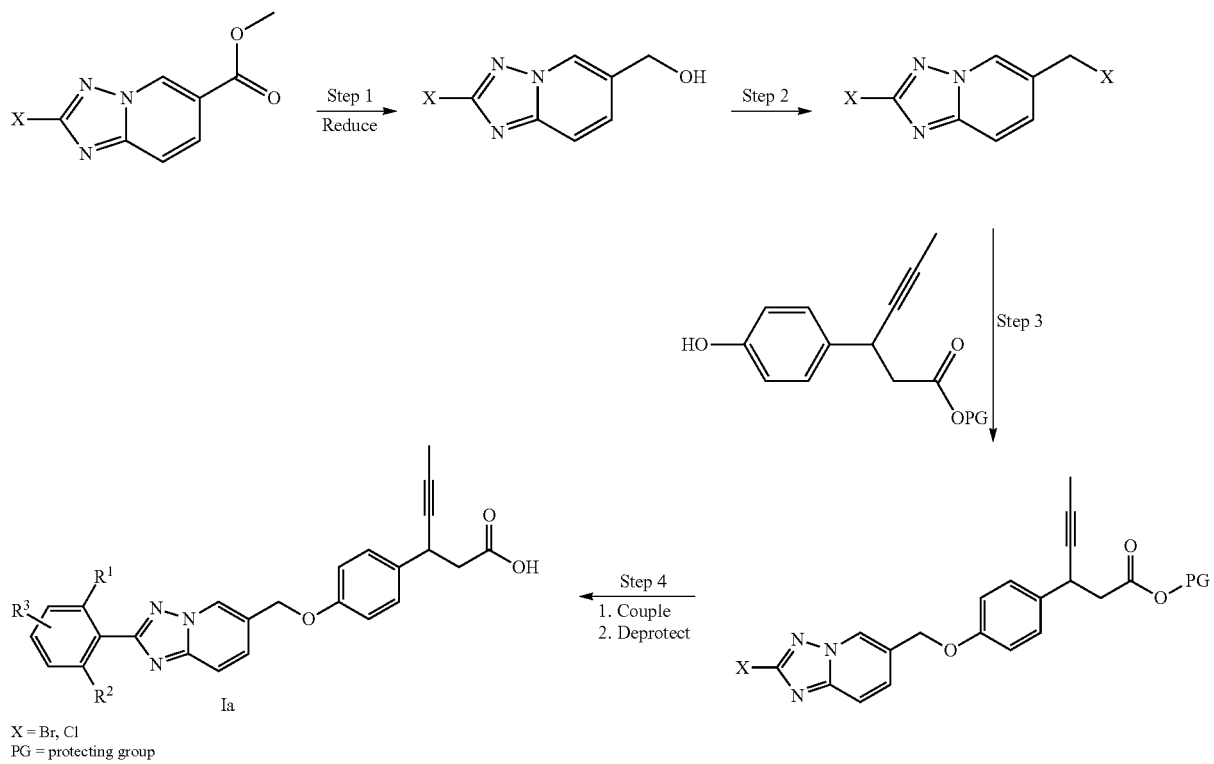

X = Br, Cl
PG = protecting group

A product of Formula Ib can be prepared in accordance with reactions as depicted in Scheme I. Scheme 1 shows the reactions of a halogen, 6-substituted [1,2,4]triazolo[1,5-a]pyridine-2-yl intermediate leading to compounds of Formula Ib. The carboxylate of the 6-substituted [1,2,4]triazolo[1,5-a]pyridine-2-yl can be reduced to the hydroxy under standard reducing conditions using a reducing agent such as excess DIBAL-H at a temperature of −78° C. in a polar aprotic solvent such as DCM to give the product of Step 1, Scheme 1. A person skilled in the art will realize there are other reducing agents such as sodium borohydride and lithium aluminum hydride that could also be used to reduce a methyl carboxylate to the hydroxy compound product of Step 1. The hydroxy product of Step 1 can be converted to a halogen such as chlorine using chlorinating agents such as $SOCl_2$ or $POCl_3$ to give the product of Step 2. Alternatively the hydroxy can be able base includes cesium carbonate, sodium carbonate, potassium carbonate, or potassium phosphate tribasic monohydrate using a non-polar solvent such as 1,4-dioxane or toluene and EtOH to give compounds of Step 4 than can be deprotected in substep 2, Step 4 under basic conditions using NaOH, LiOH, or potassium trimethylsilanote at room temperature or with heating to give compounds of Formula Ib. "PG" is a protecting group developed for an acid such as esters. Such protecting groups are well known and appreciated in the art. See. e.g., Greene and Wuts, *Protective Groups in Organic Synthesis*. Phenolic products of Step 4, substep 1 can be further alkylated under conditions well known in the art using an inorganic base such as cesium carbonate in a polar aprotic solvent such as acetonitrile to give after deprotection, compounds of Formula Ib.

Scheme 2

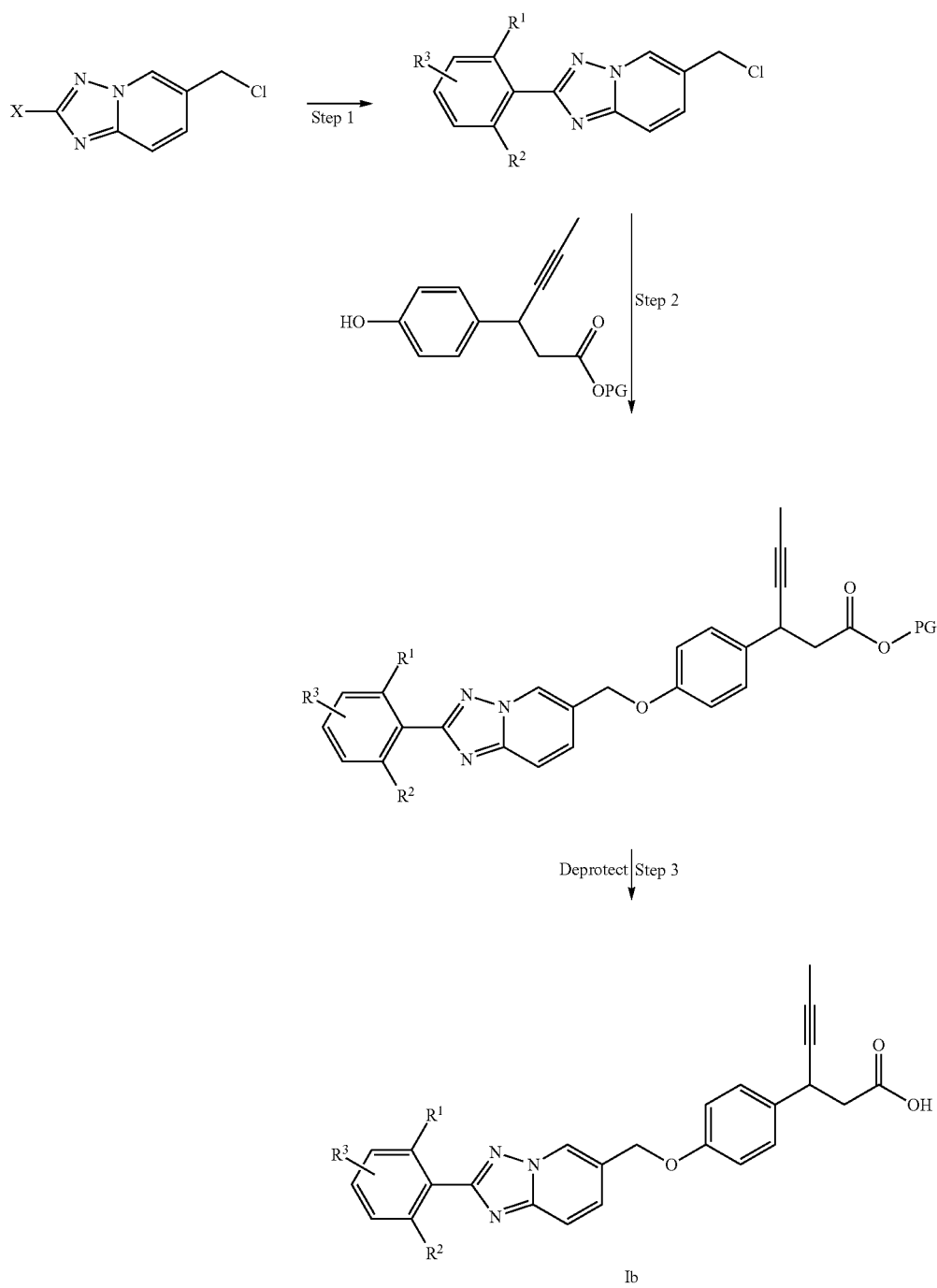

Alternatively, in Scheme 2, the product of Step 2, Scheme 1 can be coupled under Suzuki-Miyaura cross coupling conditions as described in substep 1, Step 4, Scheme 1 to give the product of Step 1, Scheme 2. The product of Step 1, Scheme 2 can then be reacted with the phenol reagent of Step 2, Scheme 2 as described in Step 3, Scheme 1 to give the product of Step 2, Scheme 2. The product of Step 2, Scheme 2 can be deprotected as described in substep 2, Step 4, Scheme 1 to give products of Formula Ib.

In an optional step, a pharmaceutically acceptable salt of a compound of Formula (I) can be formed by reaction of an appropriate acid of Formula (I) with an appropriately pharmaceutically acceptable base in a suitable solvent under standard conditions. Additionally, the formation of such salts can occur simultaneously upon hydrolysis of an ester. The formation of such salts is well known and appreciated in the art.

The following preparations and examples further illustrate the invention and represent typical synthesis of the compound of Formula (I). Unless noted to the contrary, the compounds illustrated herein are named and numbered using Accelrys Draw 4.1, IUPACNAME ACDLABS.

PREPARATION 1

Methyl 6-aminopyridine-3-carboxylate

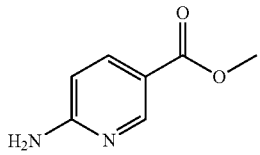

To a solution of 6-aminopyridine 3-carboxylic acid (30 g, 217.1 mmol) in methanol (30 mL) is added $H_2SO_4$ (30 mL at 0° C.) and the reaction mixture is heated to 80° C. for 16 hours. The reaction mixture is evaporated and the residue is neutralized with aqueous $NaHCO_3$ solution (50 mL), the precipitated solid is filtered and dried to give the title compound as a pale yellow solid (24 g, 72%). LCMS m/z 153(M+H)+.

PREPARATION 2

Ethyl (1E)-N-(2,4,6-trimethylphenyl)sulfonyloxy-ethanimidate

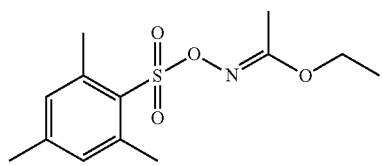 [SMILES: CCO/C(C)=N/OS(=O)(=O)c1c(C)cc(C)cc1C]

To a solution of ethyl (1E)-N-hydroxyethanimidate (8.4 g, 81.5 mmol) in DMF (20 mL) is added triethylamine (12 mL, 86.24 mmol) and the mixture is stirred for 20 minutes. 2,4,6-Trimethylbenzene-1-sulfonyl chloride (20 g, 81.5 mmol) is added and the reaction mixture is stirred at room temperature for 16 hours. The reaction mixture is quenched with water (100 mL) and extracted with EtOAc (3×100 mL). The combined organic extracts are dried over sodium sulphate, filtered, and evaporated to dryness to give the title compound as white solid (15 g, 64%). The crude material is used without further purification.

ALTERNATE PREPARATION 2

To a solution of ethyl (1E)-N-hydroxyethanimidate (250 g, 2.42 mol) in DMF (2.5 L) is added triethylamine (490.6 g, 4.85 mol) and the mixture is stirred for 20 minutes. The reaction mixture is cooled to 10° C.-15° C. and 2,4,6-trimethylbenzene-1-sulfonyl chloride (529.5 g, 2.42 mol) is added portion wise over a period of 30 minutes and the mixture is stirred at room temperature for 16 hours. The reaction mixture is quenched with water (3.5 L) and extracted with EtOAc (2×4 L). The combined organic extracts are washed with water (4×3 L), brine solution (3 L), dried over sodium sulphate, and evaporated to give the title compound as an off white solid (435 g, 63%). LCMS m/z 285.1 (M+H)+.

PREPARATION 3

Amino 2,4,6-trimethylbenzenesulfonate

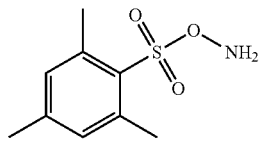

To a solution of ethyl (1E)-N-(2,4,6-trimethylphenyl)sulfonyloxyethanimidate (14 g, 49.12 mmol) in 1,4 dioxane (25 mL) is added $HClO_4$ (7.0 mL, 70% in water) at 0° C. and the reaction mixture is stirred at room temperature for 1 hour. The reaction mixture is diluted with water and extracted with DCM (2×50 mL). The combined organic extracts are dried over sodium sulphate and filtered. The crude material is used without further purification (10 g, theoretical yield).

PREPARATION 4

Methyl 1,6-diaminopyridin-1-ium-3-carboxylate; 2,4,6-trimethylbenzenesulfonate

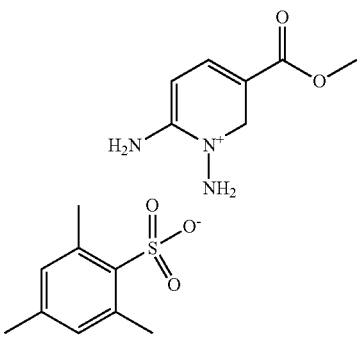

To a stirred solution of amino 2,4,6-trimethylbenzenesulfonate (10 g, 45.71 mmol) in DCM (100 mL) is added methyl 6-aminopyridine-3-carboxylate (5.55 g, 56.56 mmol). After 10 minutes, triethylamine (19.11 mL, 137.13 mmol) is added drop wise and the reaction mixture is stirred at room temperature for 16 hours. The reaction mixture is cooled to 0° C. and diethyl ether is added. The precipitated solid is filtered and dried under vacuum to give the title compound as a white solid (6.8 g, 41%). 1HNMR (DMSO-$d_6$, 400 MHz) δ 8.95 (bs, 2H), 8.63 (s, 1H), 8.11 (d, J=9.6 Hz, 1H), 7.09 (d, J=9.6 Hz, 1H) 6.89 (s, 2H), 6.73 (s, 2H), 3.85 (s, 3H), 2.48 (s, 6H), 2.16 (s, 1H).

ALTERNATE PREPARATION 4

To a stirred solution of amino 2,4,6-trimethylbenzenesulfonate (618 g, 2.87 mol) in DCM (8.5 L) is added methyl 6-aminopyridine-3-carboxylate (437.3 g, 2.87 mmol) at 10° C.-15° C. and the mixture is stirred at room temperature for 16 hours. The reaction mixture is cooled to 0° C., stirred for 20 minutes and the solid precipitate is filtered, washed with diethyl ether (2 L) and dried under vacuum to give the title compound as an off-white solid (495 g, 47%). LCMS m/z 168 (M+H)⁺.

PREPARATION 5

Methyl 2-bromo-[1,2,4]triazolo[1,5-a]pyridine-6-carboxylate

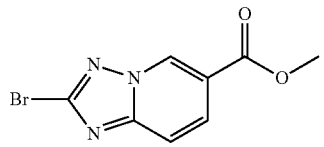

To a stirred solution of cupric bromide (13.9 g, 62.4 mmol) in acetonitrile (150 mL) is added tert-butyl nitrite (6.4 g, 62.4 mmol) at room temperature and the reaction mixture is heated to 60° C. Methyl 2-amino-[1,2,4]triazolo[1,5-a]pyridine-6-carboxylate (8.0 g, 41.6 mmol) is added portion wise and the reaction mixture is heated at the same temperature for 1 hour. The reaction mixture is quenched with water and extracted with EtOAc. The organic extract is washed with brine, dried over sodium sulphate, and evaporated to dryness. The crude material is purified by silica gel chromatography (combiflash purifier) (40 g redisep column) and is eluted with 30% EtOAc in hexane to give the title compound as an off white solid (5.1 g, 48%). LCMS m/z 363 (M+H)⁺.

PREPARATION 6

2-(4-Hydroxy-2,6-dimethyl-phenyl)-[1,2,4]triazolo[1,5-a]pyridine-6-carboxylic acid methyl ester

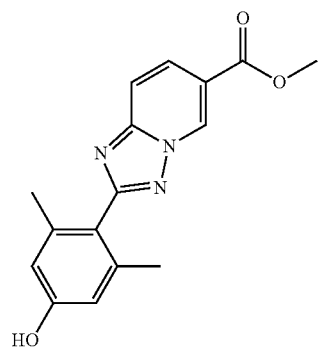 [SMILES: COC(=O)c1ccc2nc(-c3c(C)cc(O)cc3C)nn2c1]

To a stirred solution of methyl 1,6-diaminopyridin-1-ium-3-carboxylate; 2,4,6-trimethylbenzenesulfonate (8 g, 21.68 mmol) in methanol (100 mL) is added 4-hydroxy-2,6-dimethyl-benzaldehyde (3.25 g, 21.68 mmol) and triethylamine (8.77 mL, 65.04 mmol) at 0° C. and the reaction mixture is stirred at room temperature for 48 hours. The reaction mixture is concentrated and extracted with EtOAc (100 mL). The combined organic extracts are washed with water (2×100 mL), saturated ammonium chloride solution (50 mL), brine solution (50 mL), and dried over anhydrous sodium sulphate, filtered, and evaporated to dryness. The crude material is purified by silica gel chromatography (combiflash 40 g redisep Rf column) and is eluted with 40-60% EtOAc in hexane to give the title compound as a pale yellow solid (1.2 g, 18%). LCMS m/z 298 [M+H]⁺.

PREPARATION 7

2-[4-(3-Methanesulfonyl-propoxy)-2,6-dimethyl-phenyl]-[1,2,4]triazolo[1,5-a]pyridine-6-carboxylic acid methyl ester

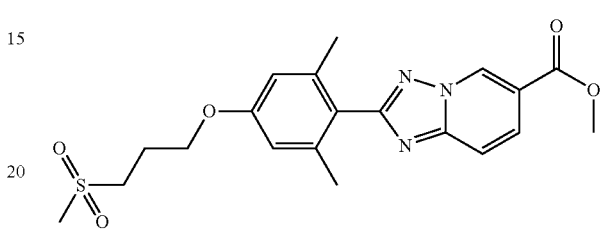

To a solution of 2-(4-hydroxy-2,6-dimethyl-phenyl)-[1,2,4]triazolo[1,5-a]pyridine-6-carboxylic acid methyl ester (0.2 g, 0.673 mmol) in acetonitrile (5 mL) is added toluene-4-sulfonic acid 3-methanesulfonyl-propyl ester (0.196 g, 0.673 mmol) and potassium carbonate (0.278 g, 2.019 mmol) at room temperature and the reaction mixture is heated at 100° C. for 16 hours. The reaction mixture is diluted with water (10 mL) and extracted with EtOAc (2×20 mL). The combined organic extracts are washed with water (10 mL), brine (10 mL), dried over anhydrous Na₂SO₄, filtered, and evaporated to dryness. The crude material is purified by silica gel chromatography (combiflash purifier 24 g redisep column) and is eluted with 40-60% EtOAc in hexane to give the title compound as a light yellow solid (198 mg, 70%). LCMS m/z 418 [M+H]⁺.

PREPARATION 8

(2-Bromo-[1,2,4]triazolo[1,5-a]pyridin-6-yl)methanol

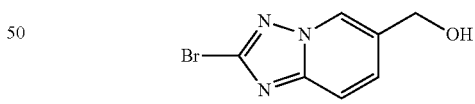

To a solution of methyl 2-bromo-[1,2,4]triazolo[1,5-a]pyridine-6-carboxylate (3.0 g, 11.7 mmol) in DCM, is added DIBAL-H (3 equivalents) drop wise at −78° C. and the reaction mixture is warmed to room temperature and stirred for 1 hour. The reaction mixture is quenched with saturated ammonium chloride solution (20 mL) and extracted with DCM (2×50 mL). The combined organic extracts are dried over sodium sulphate, and evaporated. The crude material is triturated with n-pentane to give the title compound as a yellow solid (1.5 g, 57.6%). LCMS m/z 171 (M+H)⁺.

The following compounds are prepared essentially by the method of Preparation 8.

TABLE 1

| Prep. No. | Chemical Name | Structure | LCMS (m/z) (M + H) |
|---|---|---|---|
| 9 | {2-[4-(3-Methanesulfonyl-propoxy)-2,6-dimethyl-phenyl]-[1,2,4]triazolo[1,5-a]pyridin-6-yl}-methanol | 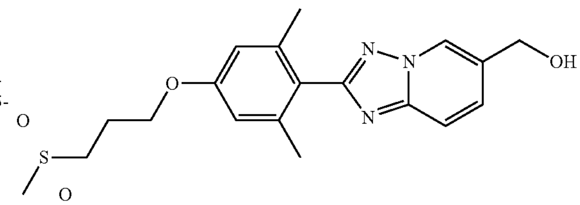 | 390 |

PREPARATION 10

2-Bromo-6-(chloromethyl)-[1,2,4]triazolo[1,5-a]pyridine

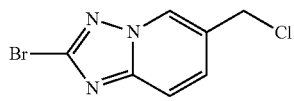 [SMILES: ClCc1ccc2nc(Br)nn2c1]

A mixture of (2-bromo-[1,2,4]triazolo[1,5-a]pyridin-6-yl)methanol (1.5 g, 6.5 mmol) and thionyl chloride (10 mL) is stirred at room temperature for 1 hour. The reaction mixture is evaporated to dryness. The residue is co-evaporated with toluene (2×20 mL) to give the title compound as a yellow solid (1.5 g, crude). LCMS m/z 247 (M+H)$^+$.

ALTERNATE PREPARATION 10

SOCl$_2$ (50 mL) is added to (2-bromo-[1,2,4]triazolo[1,5-a]pyridin-6-yl)-methanol (2.9 g, 12.69 mmol) at 0° C. and the reaction mixture is stirred at room temperature for 1 hour. The reaction mixture is cooled to 0° C., quenched with saturated sodium bicarbonate solution (100 mL), and extracted with DCM (3×30 mL). The combined organic layer is washed with brine solution, dried over sodium sulphate, filtered, and evaporated to give the title compound as a yellow solid (2.8 g, crude). LCMS m/z 246 (M+H)$^+$.

PREPARATION 11

Methyl 2-(2,6-dimethylphenyl)-[1,2,4]triazolo[1,5-a]pyridine-6-carboxylate

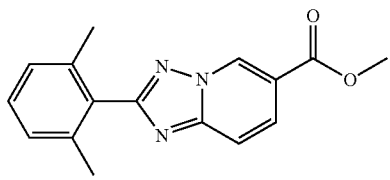 [SMILES: COC(=O)c1ccc2nc(-c3c(C)cccc3C)nn2c1]

To a solution of methyl 1,6-diaminopyridin-1-ium-3-carboxylate; 2,4,6-trimethylbenzenesulfonate (6.0 g, 16.3 mmol) in 1,4-dioxane (50 mL) is added 2,6-dimethylbenzaldehyde (1.72 g, 13.00 mmol) and the reaction mixture is heated at 90° C. for 2 hours. The reaction mixture is cooled to room temperature, 1 N KOH solution (15 mL) is added, and the mixture is stirred overnight at room temperature. The reaction mixture is diluted with water (50 mL) and extracted with EtOAc (2×100 mL). The combined organic extracts are washed with water (100 mL) and saturated brine solution (100 mL), dried over sodium sulphate, filtered, and concentrated. The crude material is purified by silica gel chromatography (combiflash) eluting with 12% EtOAc in hexanes to give the title compound as a yellow liquid (0.35 g, 16%). LCMS m/z 282 (M+H)$^+$.

ALTERNATE PREPARATION 11

To a solution of methyl 1,6-diaminopyridin-1-ium-3-carboxylat; 2,4,6-trimethylbenzenesulfonate (400 g, 1.09 mol) in methanol (5 L) is added 2,6-dimethylbenzaldehyde (146 g, 1.09 mol) and triethylamine (330.5 g, 3.27 mol) at 15° C.-20° C. and the mixture is stirred for 30 minutes. The reaction mixture is allowed to warm to room temperature and stirred for 18 hours. The solvent is removed by distillation at 50° C. The crude residue is dissolved in EtOAc (3 L) and water (4 L) and is stirred for 10 minutes. The mixture is separated and the aqueous layer is extracted with EtOAc (2×3 L). The combined organic extracts are washed with water (2×5 L) and brine solution (3 L), dried over sodium sulphate, and concentrated to obtain a brown viscous mass. The crude material is purified by silica gel column chromatography eluting with 30-50% EtOAc in hexanes to give the title compound as a pale yellow solid (125 g, 40%). LCMS m/z 282 (M+H)$^+$.

PREPARATION 12

[2-(2,6-Dimethylphenyl)-[1,2,4]triazolo[1,5-a]pyridin-6-yl]methanol

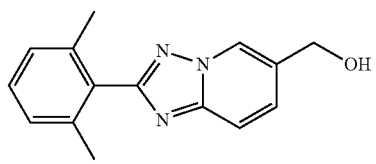 [SMILES: Cc1cccc(C)c1-c1nc2ccc(CO)cn2n1]

To a solution of methyl 2-(2,6-dimethylphenyl)-[1,2,4]triazolo[1,5-a]pyridine-6-carboxylate (0.35 g, 1.24 mmol) in DCM (20 mL), DiBAL-H (1 M solution in toluene, 4.98 mL, 4.98 mmol) is added drop wise at 0° C. The reaction mixture is warmed to room temperature and stirred for 2 hours. The reaction is quenched with aqueous NH$_4$Cl solution and extracted with EtOAc (4×50 mL). The combined extracts are dried over sodium sulphate, filtered, and concentrated. The crude material is purified by silica gel chromatography (combiflash) eluting with 50% EtOAc in hexanes. The product is concentrated to give the title compound as a transparent liquid (0.18 g, 57%). LCMS m/z 254 (M+H)$^+$.

PREPARATION 13

6-(Chloromethyl)-2-(2,6-dimethylphenyl)-[1,2,4]triazolo[1,5-a]pyridine

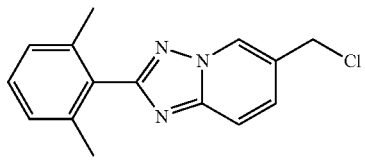 [SMILES: Cc1cccc(C)c1-c1nc2ccc(CCl)cn2n1]

A solution of [2-(2,6-dimethylphenyl)-[1,2,4]triazolo[1,5-a]pyridin-6-yl]methanol (0.17 g, 0.67 mmol) in SOCl$_2$ (2.0 mL) is stirred for 2 hours at room temperature. The reaction mixture is evaporated to dryness and co-distilled with toluene to give the title compound as a yellow solid (0.198 g, 100% crude) which is used without further purification. LCMS m/z 272 (M+H)$^+$.

PREPARATION 14

6-(Bromomethyl)-2-(2,6-dimethylphenyl)-[1,2,4]triazolo[1,5-a]pyridine

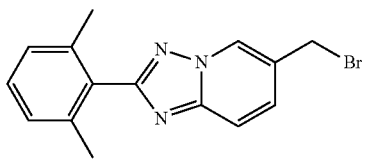 [SMILES: Cc1cccc(C)c1-c1nc2ccc(CBr)cn2n1]

To a solution of (2-(2,6-dimethylphenyl)-[1,2,4]triazolo[1,5-a]pyridin-6-yl)methanol (148 g, 0.584 mol) in DCM (2.96 L) is added PBr$_3$ (237.3 g, 0.877 mol) at −40° C. The reaction mixture is allowed to warm to temperature and then stirred for a further for 2 hours at room temperature. The reaction is cooled to 0° C., quenched with ice cold water (1.5 L) and saturated sodium bicarbonate solution is added to adjust the pH ~7.5 to 8. The mixture is diluted with DCM (2 L), the aqueous layer is separated and extracted with DCM (3 L). The organic extracts are combined, washed with water (2×3 L) and brine solution (3 L), dried the organic extracts over sodium sulphate, filtered and evaporated to dryness to give the title compound (140 g, 76%). LCMS m/z 316/318 $^{79}$Br/$^{81}$Br (M+H)$^+$.

ALTERNATE PREPARATION 14

To a solution of (2-(2,6-dimethylphenyl)-[1,2,4]triazolo[1,5-a]pyridin-6-yl)methanol (0.2 g, 0.79 mmol) in DCM (10 mL) is added PBr$_3$ (0.11 mL, 1.18 mmol) at −40° C. and the reaction mixture is stirred at room temperature for 2 hours. The reaction mixture is cooled to 0° C., quenched with ice cold water (5 mL), 10% sodium bicarbonate solution (10 mL) is added, and the mixture is extracted with DCM (3×20 mL). The combined organic extracts are washed with brine solution, dried over sodium sulphate, filtered, and evaporated to dryness to give the title compound (0.17 g, crude). LCMS m/z $^{79}$Br/$^{81}$Br 316/318 (M+H)$^+$.

The following compound is prepared essentially by the method of Alternate Preparation 14.

TABLE 2

| Prep. No. | Chemical Name | Structure | LCMS (m/z) (M + 1) |
|---|---|---|---|
| 15 | 6-Bromomethyl-2-[4-(3-methanesulfonyl-propoxy)-2,6-dimethyl-phenyl]-[1,2,4]triazolo[1,5-a]pyridine | 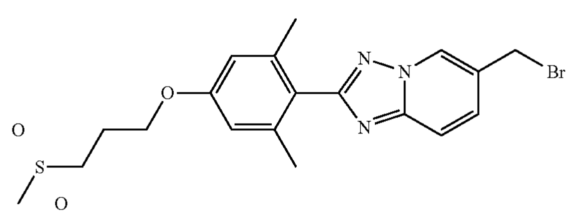 | ($^{79}$Br/$^{81}$Br) 452/454 |

PREPARATION 16

Ethyl (3S)-3-[4-[(2-bromo-[1,2,4]triazolo[1,5-a]pyridin-6-yl)methoxy]phenyl]hex-4-ynoate

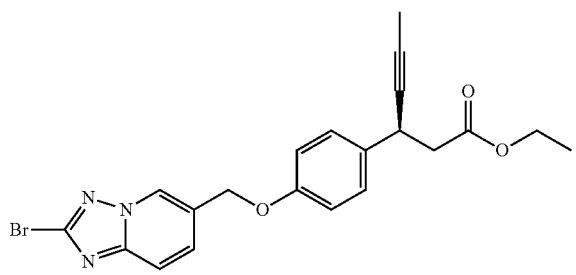 [SMILES: CC#C[C@@H](CC(=O)OCC)c1ccc(OCc2ccc3nc(Br)nn3c2)cc1]

To a stirred solution of (S)-ethyl 3-(4-hydroxyphenyl)hex-4-ynoate (1.4 g, 6.09 mmol) in DMF, is added cesium carbonate (5.9 g, 18.1 mmol) and 2-bromo-6-(chloromethyl)-[1,2,4]triazolo[1,5-a]pyridine (1.5 g, 6.09 mmol) and the reaction mixture is stirred at room temperature for 2 hours. The reaction mixture is quenched with ice cold water and extracted with EtOAc (2×200 mL). The organic extract is washed with brine (2×30 mL), dried over sodium sulphate, and concentrated. The crude material is purified by silica gel chromatography (combiflash purifier 10 g redisep column) eluting with 25% EtOAc in hexane to give the title compound as a yellow sticky oil (1.4 g, 54%). LCMS m/z 442 (M+H)$^+$.

ALTERNATE PREPARATION 16

A mixture of 2-bromo-6-chloromethyl-[1,2,4]triazolo[1,5-a]pyridine (2.8 g, 11.39 mmol), (S)-ethyl 3-(4-hydroxyphenyl)hex-4-ynoate (2.6 g, 11.359 mmol) and cesium carbonate (11.10 g, 34.07 mmol) in acetonitrile (50 mL) is stirred at room temperature overnight. The reaction mixture is diluted with water (50 mL) and extracted with EtOAc (2×50 mL). The combined organic extracts are washed with saturated brine solution (20 mL), dried over sodium sulphate, filtered, and evaporated to dryness. The crude material is purified by silica gel chromatography (combiflash purifier 40 g redisep column) and is eluted in 42% EtOAc in hexane to give the title compound as a brown liquid (4 g, 80%). LCMS m/z 442 (M+H)$^+$.

The following compound is prepared essentially by the method of Alternate Preparation 16 using 6-bromomethyl-2-[4-(3-methanesulfonyl-propoxy)-2,6-dimethyl-phenyl]-[1,2,4]triazolo[1,5-a]pyridine as the starting material with (S)-3-(4-hydroxy-phenyl)-hex-4-ynoic acid ethyl ester.

TABLE 3

| Prep. No. | Chemical Name | Structure | LCMS (m/z) (M + 1) |
|---|---|---|---|
| 17 | (S)-3-(4-{2-[4-(3-Methanesulfonyl-propoxy)-2,6-dimethyl-phenyl]-[1,2,4]triazolo[1,5-a]pyridin-6-ylmethoxy}-phenyl)-hex-4-ynoic acid ethyl ester | 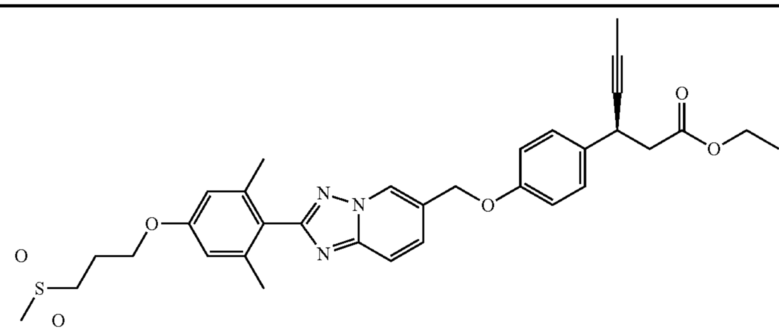 | 604 |

PREPARATION 18

(S)-3-(4-{2-[4-(3-Methanesulfonyl-propoxy)-2-methyl-phenyl]-[1,2,4]triazolo[1,5-a]pyridin-6-ylmethoxy}-phenyl)-hex-4-ynoic acid ethyl ester

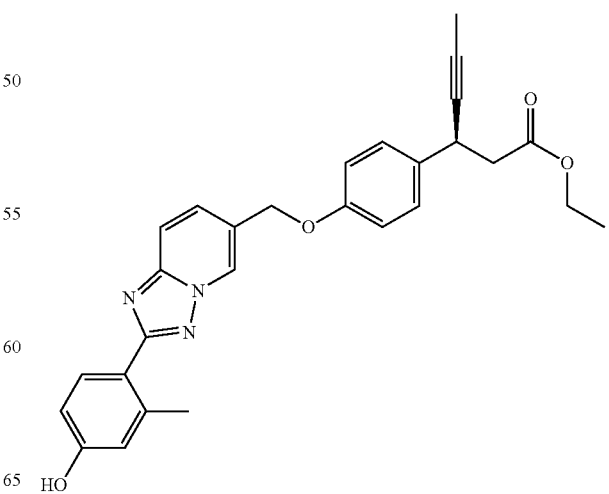

To a stirred solution of ethyl (3S)-3-[4-[(2-bromo-[1,2,4]triazolo[1,5-a]pyridin-6-yl)methoxy]phenyl]hex-4-ynoate (0.5 g, 1.13 mmol) and 4-hydroxy-2-methylbenzeneboronic acid (0.206 g, 1.35 m mL) in 1,4-dioxane (10 mL), is added a solution of 2 M potassium carbonate (1.69 mL, 3.39 mmol). The mixture is purged with nitrogen for 20 minutes, Pd(PPh₃)₂Cl₂ (0.039 g, 0.056 mmol) is added and the mixture is irradiated with microwave radiation for 4 hours at 100° C. The reaction mixture is filtered through diatomaceous earth and washed with EtOAc (10 mL). The filtrate is washed with cold water (2×20 mL) and brine solution, dried over sodium sulphate, and evaporated under reduced pressure. The residue is purified by silica gel chromatography (combiflash) eluting with 15% EtOAc in hexane to give the title compound as a yellow syrup (0.3 g, 56.6%). LCMS m/z 470 (M+H)⁺.

PREPARATION 19

(S)-3-(4-{2-[4-(3-Methanesulfonyl-propoxy)-2-methyl-phenyl]-[1,2,4]triazolo[1,5-a]pyridin-6-ylmethoxy}-phenyl)-hex-4-ynoic acid ethyl ester

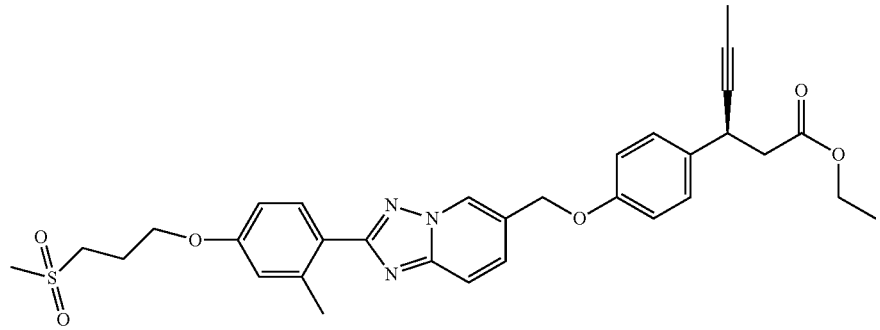 [SMILES: CC#C[C@@H](CC(=O)OCC)c1ccc(OCc2ccc3nc(-c4ccc(OCCCS(C)(=O)=O)cc4C)nn3c2)cc1]

To a stirred solution of (S)-3-(4-{2-[4-(3-methanesulfonyl-propoxy)-2-methyl-phenyl]-[1,2,4]triazolo[1,5-a]pyridin-6-ylmethoxy}-phenyl)-hex-4-ynoic acid ethyl ester (0.3 g, 0.630 mmol) and toluene-4-sulfonic acid 3-methanesulfonyl-propyl ester (0.18 g, 0.634 mmol) in acetonitrile (10 mL) is added potassium carbonate (0.26 g, 1.89 mmol) at room temperature and the reaction mixture is heated at 90° C. overnight. The reaction mixture is filtered through diatomaceous earth, washed with EtOAc (10 mL), and the filtrate is evaporated to dryness. The residue is dissolved in EtOAc (10 mL), washed with water (2×30 mL), brine solution, dried over sodium sulphate, and evaporated under reduced pressure. The crude compound is purified by silica gel (combiflash purifier) and is eluted with 50% EtOAc in hexane to give the title compound as a yellow solid (0.12 g, 32.3%). LCMS m/z 590 (M+H)⁺.

PREPARATION 20

(S)-3-{4-[2-(4-Hydroxy-phenyl)-[1,2,4]triazolo[1,5-a]pyridin-6-ylmethoxy]-phenyl}-hex-4-ynoic acid ethyl ester

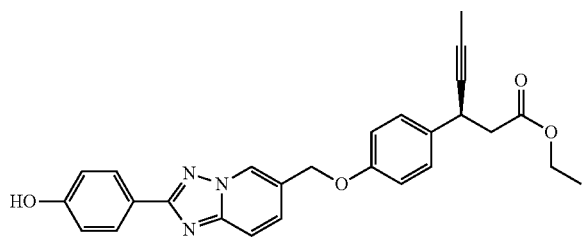 [SMILES: CC#C[C@@H](CC(=O)OCC)c1ccc(OCc2ccc3nc(-c4ccc(O)cc4)nn3c2)cc1]

To a stirred solution of ethyl (3S)-3-[4-[(2-bromo-[1,2,4]triazolo[1,5-a]pyridin-6-yl)methoxy]phenyl]hex-4-ynoate (1.0 g, 2.2 mmol) and 4-hydroxy phenyl boronic acid (0.37 g, 2.7 mmol) in 1,4-dioxane (30 mL) is added K₂CO₃ (0.91 g, 6.6 mmol). The mixture purged with nitrogen for 10 minutes. Pd(PPh₃)₂Cl₂ (0.14 g, 0.2 mmol) is added and the mixture is heated at 100° C. for 12 hours. The reaction mixture is cooled to room temperature, filtered through diatomaceous earth, and washed with EtOAc (2×10 mL). The filtrate is dried over anhydrous sodium sulphate, filtered, and concentrated to dryness. The crude material is purified by silica gel chromatography (combiflash using 24 g redisep column) eluting with 15-20% EtOAc/hexane to give the title compound (0.75 g, 73.52%). LCMS m/z 456.2 (M+H)⁺.

PREPARATION 21

(S)-3-(4-{2-[4-(2-Methoxy-ethoxy)-phenyl]-[1,2,4]triazolo[1,5-a]pyridin-6-ylmethoxy}-phenyl)-hex-4-ynoic acid ethyl ester

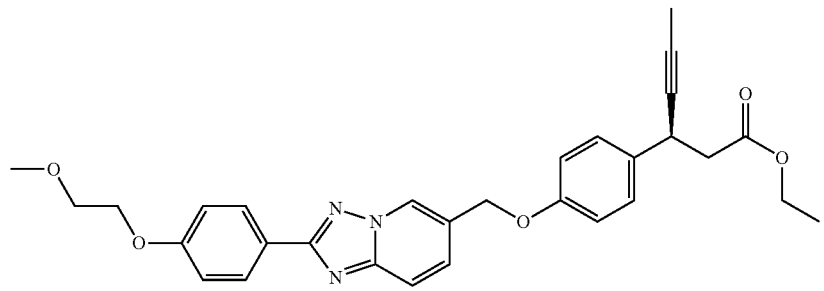 [SMILES: CC#C[C@@H](CC(=O)OCC)c1ccc(OCc2ccc3nc(-c4ccc(OCCOC)cc4)nn3c2)cc1]

To a stirred solution (S)-3-{4-[2-(4-hydroxy-phenyl)-[1,2,4]triazolo[1,5-a]pyridin-6-ylmethoxy]-phenyl}-hex-4-ynoic acid ethyl ester (0.250 g, 0.585 mmol) and 1-bromo-2-methoxy-ethane (0.22 mL, 2.34 mmol) in acetonitrile (10 mL) is added cesium carbonate (0.381 g, 1.17 mmol) at room temperature and the reaction mixture is stirred at room temperature overnight. The reaction mixture is filtered through diatomaceous earth and washed with EtOAc (20 mL), and the filtrate is concentrated to dryness. The residue is dissolved in EtOAc (30 mL), washed with water (2×30 mL), brine solution (30 mL), dried over sodium sulphate, and evaporated under reduced pressure. The crude compound is purified by silica gel (combiflash purifier) and is eluted with 17-19% EtOAc in hexane to give the title compound as a white semi solid (0.190 g, 64%). LCMS m/z 514 (M+H)$^+$.

PREPARATION 22

(S)-3-(4-{2-[4-(3-Hydroxy-3-methyl-butoxy)-phenyl]-[1,2,4]triazolo[1,5-a]pyridin-6-ylmethoxy}-phenyl)-hex-4-ynoic acid ethyl ester

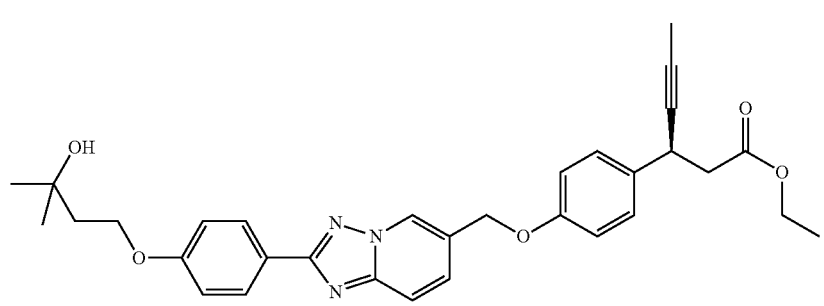 [SMILES: CC#C[C@@H](CC(=O)OCC)c1ccc(OCc2ccc3nc(-c4ccc(OCCC(C)(C)O)cc4)nn3c2)cc1]

To a stirred solution of (S)-3-{4-[2-(4-hydroxy-phenyl)-[1,2,4]triazolo[1,5-a]pyridin-6-ylmethoxy]-phenyl}-hex-4-ynoic acid ethyl ester (0.2 g, 0.43 mmol) in acetonitrile (20 mL) is added 4-bromo-2-methyl-butan-2-ol (0.14 g, 0.87 mmol) and cesium carbonate (0.41 g, 1.2 mmol) and the reaction mixture is stirred at room temperature for 2 hours.

The reaction mixture is filtered and evaporated to dryness. The crude material is purified by silica gel chromatography (combiflash purifier 24 g redisep column) and is eluted with 15-20% EtOAc in hexane to give the title compound (0.23 g, 100%). LCMS m/z 542 (M+H)⁺.

PREPARATION 23

(S)-3-{4-[2-(4-Difluoromethoxy-phenyl)-[1,2,4]triazolo[1,5-a]pyridin-6-ylmethoxy]-phenyl}-hex-4-ynoic acid ethyl ester

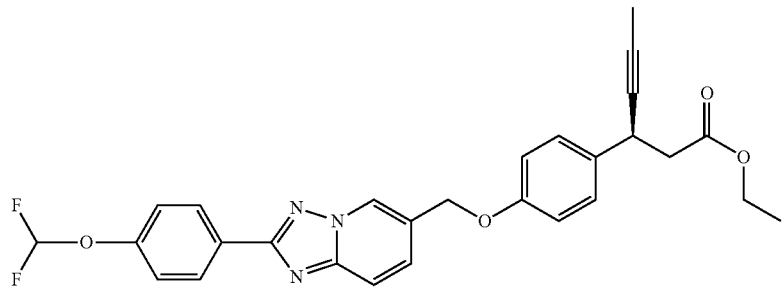 [SMILES: CC#C[C@@H](CC(=O)OCC)c1ccc(OCc2ccc3nc(-c4ccc(OC(F)F)cc4)nn3c2)cc1]

A mixture of (S)-3-{4-[2-(4-hydroxy-phenyl)-[1,2,4]triazolo[1,5-a]pyridin-6-ylmethoxy]-phenyl}-hex-4-ynoic acid ethyl ester (0.25 g, 0.54 mmol) in DMF (10 mL) is added sodium chloro difluoro acetate (0.142 g, 1.09 mmol) and cesium carbonate (0.354 g, 1.09 mmol) at 0° C. and the reaction mixture is heated at 80° C. for 4 hours. The reaction mixture is diluted with ice cold water (50 mL) and extracted with EtOAc (2×20 mL). The combined organic extracts are washed with saturated brine solution (20 mL), dried over sodium sulphate, filtered, and evaporated to dryness. The crude material is purified by silica gel (combiflash purifier 40 g redisep column) and is eluted with 45% EtOAc in hexane to give the title compound as a colorless semi solid (0.15 g, 55.5%). LCMS m/z 506 (M+H)⁺.

PREPARATION 24

(S)-3-{4-[2-(4-Cyano-phenyl)-[1,2,4]triazolo[1,5-a]pyridin-6-ylmethoxy]-phenyl}-hex-4-ynoic acid ethyl ester

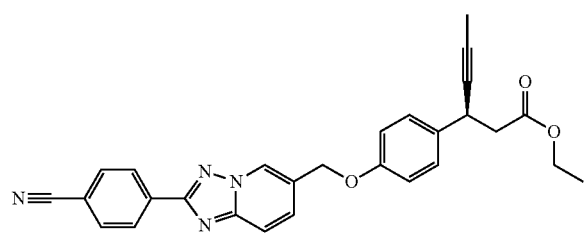 [SMILES: CC#C[C@@H](CC(=O)OCC)c1ccc(OCc2ccc3nc(-c4ccc(C#N)cc4)nn3c2)cc1]

To a stirred solution of ethyl (3S)-3-[4-[(2-bromo-[1,2,4]triazolo[1,5-a]pyridin-6-yl)methoxy]phenyl]hex-4-ynoate (0.25 g, 0.57 mmol) and 4-(4,4,5,5-tetramethyl-[1,3,2]dioxaborolan-2-yl)-benzonitrile (0.14 g, 0.5 mmol) in dioxane (115 mL) is added K₂CO₃ (0.15 g, 1.134 mmol). The mixture is purged with argon for 30 minutes, Pd(PPh₃)₄ (0.032 g, 0.027 mmol) is added and the mixture is heated at 100° C. for 5 hours. The reaction mixture is cooled to room temperature, filtered through diatomaceous earth. The filtrate is evaporated under reduced pressure and concentrated to dryness. The crude material is purified by silica gel chromatography (combiflash) eluting with 30% EtOAc/hexane to give the title compound as a brown liquid (0.170 g, 68.75%). LCMS m/z 464 (M+H).

PREPARATION 25

(S)-3-{4-[2-(4-Isopropyl-phenyl)-[1,2,4]triazolo[1,5-a]pyridin-6-ylmethoxy]-phenyl}-hex-4-ynoic acid ethyl ester

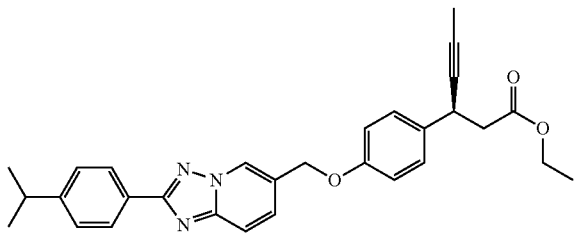 [SMILES: CC#C[C@@H](CC(=O)OCC)c1ccc(OCc2ccc3nc(-c4ccc(C(C)C)cc4)nn3c2)cc1]

To a stirred solution of ethyl (3S)-3-[4-[(2-bromo-[1,2,4]triazolo[1,5-a]pyridin-6-yl)methoxy]phenyl]hex-4-ynoate (0.3 g, 0.67 mmol) and 4-isopropyl-phenylboronic acid (0.24 g, 1.0 mmol) in toluene (16 mL) and EtOH (4 mL) is added 2 M K₂CO₃ (0.6 mL, 1.34 mmol). The mixture is purged with argon for 30 minutes. Pd(PPh₃)₄ (0.077 g, 0.067 mmol) is added and the mixture is heated at 100° C. overnight. The reaction mixture is cooled to room temperature, filtered through diatomaceous earth. The filtrate is diluted with water (30 mL) and extracted with EtOAc (2×20 mL). The combined organic extracts are washed with saturated brine solution (20 mL), dried over sodium sulphate, filtered, and concentrated to dryness. The crude material is purified by silica gel chromatography (combiflash using 24 g redisep column) eluting with 45% EtOAc/hexane to give the title compound as a brown liquid (0.22 g, 68.75%). LCMS m/z 481 (M+H)+.

PREPARATION 26

Ethyl (3S)-3-[4-[[2-(2,6-dimethylphenyl)-[1,2,4]triazolo[1,5-a]pyridin-6-yl]methoxy]phenyl]hex-4-ynoate

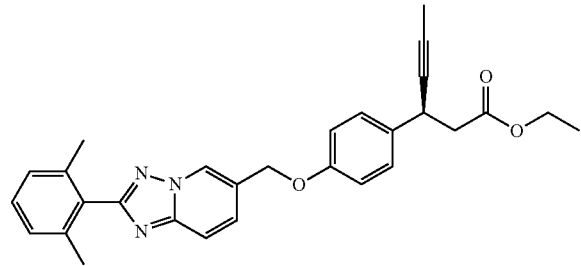 [SMILES: CC#C[C@@H](CC(=O)OCC)c1ccc(OCc2ccc3nc(-c4c(C)cccc4C)nn3c2)cc1]

To a solution of (S)-ethyl 3-(4-hydroxyphenyl)hex-4-ynoate (WO05/086661) (0.2 g, 0.87 mmol) in DMF (20 mL) is added Cs₂CO₃ (0.84 g, 2.59 mmol) and 6-(chloromethyl)-2-(2,6-dimethylphenyl)-[1,2,4]triazolo[1,5-a]pyridine (0.187 g, 0.69 mmol). The reaction mixture is stirred at room temperature for 16 hours. The reaction mixture is poured into ice cold water and extracted with EtOAc (3×50 mL). The combined organic extracts are washed with water (2×50 mL), brine (50 mL), dried over anhydrous Na₂SO₄, filtered, and evaporated to dryness. The crude material is purified by combiflash silica gel chromatography eluting with 13% EtOAc in hexane to give the title compound as colourless liquid (0.225 g, 55%). LCMS m/z 468 (M+H)+.

ALTERNATE PREPARATION 26

To a solution of (S)-ethyl 3-(4-hydroxyphenyl) hex-4-ynoate (14.69 g, 63.25 mmol) in DMF (200 mL) is added Cs₂CO₃ (61.82 g, 189.75 mmol) at 10° C.-15° C. and the mixture is stirred for 15 min. 6-(Bromomethyl)-2-(2,6-dimethylphenyl)-[1,2,4]triazolo[1,5-a]pyridine (20 g, 63.25 mmol) is added and the mixture is stirred at room temperature for 16 hours. The reaction mixture is quenched with cold water (400 mL) and extracted with EtOAc (2×200 mL). The combined organic layers are washed with water (4×600 mL), brine solution (500 mL), dried over sodium sulphate, and evaporated. The crude product is purified by silica gel chromatography eluting with 30-50% EtOAc in hexanes to give the title compound as a pale yellow solid (17 g, 57%). LCMS m/z 467 (M+H)+.

EXAMPLE 1

(3S)-3-[4-[[2-(2,6-Dimethylphenyl)-[1,2,4]triazolo[1,5-a]pyridin-6-yl]methoxy]phenyl]hex-4-ynoic acid

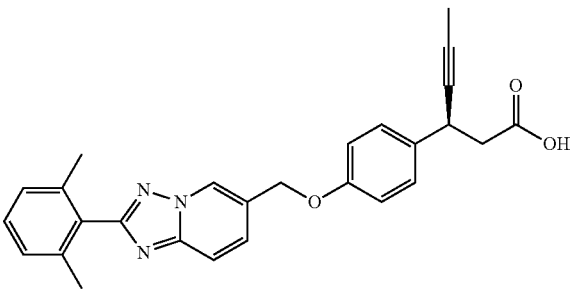 [SMILES: CC#C[C@@H](CC(=O)O)c1ccc(OCc2ccc3nc(-c4c(C)cccc4C)nn3c2)cc1]

To a solution of ethyl (3S)-3-[4-[[2-(2,6-dimethylphenyl)-[1,2,4]triazolo[1,5-a]pyridin-6-yl]methoxy]phenyl]hex-4-ynoate (0.22 g, 0.47 mmol) in EtOH (20 mL) is added 5 N NaOH (0.3 mL) and the reaction mixture is stirred at 80° C. in a microwave instrument for 30 minutes. The reaction mixture is evaporated to dryness, diluted with water, and acidified with 6 N HCl solution to pH ~3. The precipitated solid is filtered, washed with n-pentane, and dried to give the title compound as a white solid (0.155 g, 75%). LCMS m/z 440 (M+H)+.

ALTERNATE PREPARATION

Example 1

To a solution of ethyl (3S)-3-[4-[[2-(2,6-dimethylphenyl)-[1,2,4]triazolo[1,5-a]pyridin-6-yl]methoxy]phenyl]hex-4-ynoate (16 g, 34.22 mmol) in ethanol (160 mL) is added aqueous 5 N NaOH (2.73 g, 68.44 mmol in 16 mL water) drop wise at room temperature and the reaction mixture is stirred for 16 hours. The reaction mixture is evaporated to dryness, the residue is dissolved in water (300 mL), washed with diethyl ether (2×200 mL), and the organic extract is discarded. The aqueous layer is cooled to 10° C.-15° C., acidified with saturated citric acid solution to pH~5, and extracted with DCM (2×300 mL). The combined organic extracts are washed with water (2×500 mL), brine solution (500 mL), dried over Na₂SO₄, filtered, and evaporated to dryness to give the title compound as an off-white solid (14 g, 93%). LCMS m/z 440 (M+H)+.

The products from other batches, prepared as in Alternate Preparation of Example 1, are mixed with the product from Alternate Preparation Example 1 DCM (5 L) and warmed to 40° C. to get a clear solution. Then the solvent is evaporated to give an off-white solid. The possibility of trapped DCM is a concern, thus EtOAc (7.5 L) is charged and the resulting mixture is warmed to 65° C. to get a clear solution (~30 minutes). The solvent is evaporated and the resulting solid is dried under vacuum at 50° C. to obtain the desired product as an off-white solid. LCMS m/z 440 (M+H)+.

Form II Seed Crystal

Example 1

A saturated ethanol solution of (3S)-3-[4-[[2-(2,6-Dimethylphenyl)-[1,2,4]triazolo[1,5-a]pyridin-6-yl]methoxy]phenyl]hex-4-ynoic acid is filtered through 0.22 µm nylon syringe filter into a clean vessel. Slow solvent evaporation at 25° C. results in Form II seed crystals of Example 1.

Crystalline Form II (3S)-3-[4-[[2-(2,6-Dimethylphenyl)-[1,2,4]triazolo[1,5-a]pyridin-6-yl]methoxy]phenyl]hex-4-ynoic acid (3S)-3-[4-[[2-(2,6-Dimethylphenyl)-[1,2,4]triazolo[1,5-a]pyridin-6-yl]methoxy]phenyl]hex-4-ynoic acid can be prepared as a crystalline anhydrous Form II by dissolving (3S)-3-[4-[[2-(2,6-Dimethylphenyl)-[1,2,4]triazolo[1,5-a]pyridin-6-yl]methoxy]phenyl]hex-4-ynoic acid (580 mg, 132 mmol) in EtOH (1.2 mL) while stirring the mixture at 80° C. for 10 minutes. The solution is filtered and cooled to 70° C. at which point seeds of Form II are introduced. The mixture is then slowly cooled to ambient temperature while stirring overnight. The resulting solid plug is loosened with the addition of heptane (600 µL) and the solids are recovered by vacuum filtration and dried under vacuum at 60° C. to give the crystalline title product (438 mg, 75.5%).

X-Ray Powder Diffraction

Example 1, Form II

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of (3S)-3-[4-[[2-(2,6-Dimethylphenyl)-[1,2,4]triazolo[1,5-a]pyridin-6-yl]methoxy]phenyl]hex-4-ynoic acid Form II is characterized by an XRD pattern using CuKa radiation as having diffraction peaks (2-theta values) as described in Table 4 below. Specifically the pattern contains a peak at 17.55 in combination with one or more of the peaks selected from the group consisting of 5.82, 10.78, 19.65, 21.31, and 24.33 with a tolerance for the diffraction angles of 0.2 degrees.

X-ray powder diffraction peaks of (3S)-3-[4-[[2-(2,6-Dimethylphenyl)-[1,2,4]triazolo[1,5-a]pyridin-6-yl]methoxy]phenyl]hex-4-ynoic acid

Form II

TABLE 4

| Peak | Angle (2-Theta °) +/− 0./2° | Relative Intensity (% of most intense peak) |
|---|---|---|
| 1 | 5.82 | 50 |
| 2 | 9.70 | 22 |
| 3 | 10.78 | 41 |
| 4 | 11.05 | 26 |
| 5 | 11.67 | 26 |
| 6 | 12.13 | 21 |
| 7 | 12.86 | 28 |
| 8 | 14.61 | 34 |
| 9 | 15.90 | 26 |
| 10 | 16.66 | 25 |
| 11 | 17.55 | 100 |
| 12 | 18.38 | 44 |
| 13 | 19.17 | 23 |
| 14 | 19.65 | 51 |
| 15 | 20.11 | 37 |
| 16 | 21.31 | 69 |
| 17 | 23.43 | 44 |
| 18 | 24.33 | 55 |
| 19 | 24.94 | 32 |
| 20 | 25.92 | 37 |
| 21 | 26.40 | 37 |
| 22 | 27.21 | 24 |
| 23 | 27.72 | 24 |
| 24 | 29.45 | 26 |

Crystalline Form I

Example 1

(3S)-3-[4-[[2-(2,6-Dimethylphenyl)-[1,2,4]triazolo[1,5-a]pyridin-6-yl]methoxy]phenyl]hex-4-ynoic acid (0.102 g, 0.232 mmol) is dissolved in isopropylacetate (2 mL) at 80° C. The heat is removed and the sample allowed to come to room temperature resulting in crystal formation. Heptane (3 mL) is added in increments of 1 mL to give a cloudy and gumming solution. The sample is stirred and heated at 90° C. for 1 hour to give a bright white solid of birefringent blades/plates that is vacuum filtered and dried under vacuum for 10 minutes.

Alternate Form I Crystal

Example 1

(3S)-3-[4-[[2-(2,6-Dimethylphenyl)-[1,2,4]triazolo[1,5-a]pyridin-6-yl]methoxy]phenyl]hex-4-ynoic acid (44 g, 0.10 mol) is suspended in ethanol (1.1 L) and stirred at 60° C. resulting in a clear solution. The temperature is raised to 70° C. and water is slowly added (638 mL) and the mixture is stirred for 30 minutes at this temperature and then cooled to 5°

C. with stirring for 1 hour 30 minutes. The mixture is heated to 55° C. for about 10 minutes and cooled to 15° C. The mixture is stirred at 14 hours at 15° C. White crystals are filtered under vacuum and air dried to give the title compound (24.1 g, 55%) that is further dried under vacuum at 40° C.

X-Ray Powder Diffraction

Example 1, Form II

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of (3S)-3-[4-[[2-(2,6-Dimethylphenyl)-[1,2,4]triazolo[1,5-a]pyridin-5-yl]methoxy]phenyl] hex-4-ynoic acid Form I is characterized by an XRD pattern using CuKa radiation as having diffraction peaks (2-theta values) as described in Table 5 below. Specifically the pattern contains a peak at 17.70 in combination with one or more of the peaks selected from the group consisting of 4.92, 13.33, 18.44, 20.27, and 23.36 with a tolerance for the diffraction angles of 0.2 degrees.

X-ray powder diffraction peaks of (3S)-3-[4-[[2-(2,6-Dimethylphenyl)-[1,2,4]triazolo[1,5-a]pyridin-6-yl] methoxy]phenyl]hex-4-ynoic acid Form I

TABLE 5

| Peak | Angle (2-Theta °) | Intensity (%) |
| --- | --- | --- |
| 1 | 4.92 | 45 |
| 2 | 8.53 | 10 |
| 3 | 8.80 | 9 |
| 4 | 9.89 | 18 |
| 5 | 10.08 | 8 |
| 6 | 13.33 | 28 |
| 7 | 13.78 | 8 |
| 8 | 16.09 | 12 |
| 9 | 17.70 | 100 |
| 10 | 18.44 | 47 |
| 11 | 20.27 | 48 |
| 12 | 21.53 | 8 |
| 13 | 22.10 | 16 |
| 14 | 23.36 | 27 |
| 15 | 23.50 | 27 |
| 16 | 24.78 | 13 |
| 17 | 25.44 | 16 |
| 18 | 25.70 | 15 |
| 19 | 27.16 | 13 |
| 20 | 27.89 | 9 |
| 21 | 28.46 | 8 |

The following compounds are prepared essentially as described for Alternate Preparation Example 1. The reactions are stirred at room temperature from 2-4 hours. The product can be collected as a precipitate when acidified with saturated citric acid or extracted with DCM filtered, and concentrated to dryness.

TABLE 6

| Ex. No. | Chemical Name | Structure | LCMS (m/z) (M + H) |
| --- | --- | --- | --- |
| 2[a] | (3S)-3-[4-[[2-[2-Methyl-4-[3-(methylsulfonyl)propoxy]phenyl]1,2,4]triazolo[1,5-a]pyridin-6-yl]methoxy]phenyl]hex-4-ynoic acid | 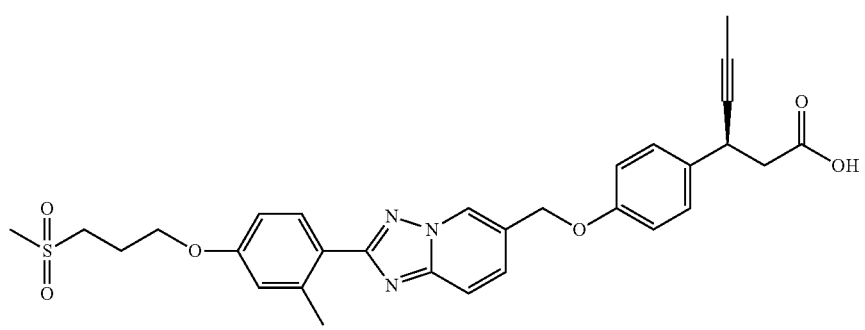 [SMILES: CC#C[C@@H](CC(=O)O)c1ccc(OCc2ccc3nc(-c4ccc(OCCCS(C)(=O)=O)cc4C)nn3c2)cc1] | 562 |

TABLE 6-continued

| Ex. No. | Chemical Name | Structure | LCMS (m/z) (M + H) |
|---|---|---|---|
| 3[a] | (3S)-3-[4-[[2-[4-(2-Methoxyethoxy)pheny][1,2,4]triazolo[1,5-a]pyridin-6-yl]methoxy]phenyl]hex-4-ynoic acid | 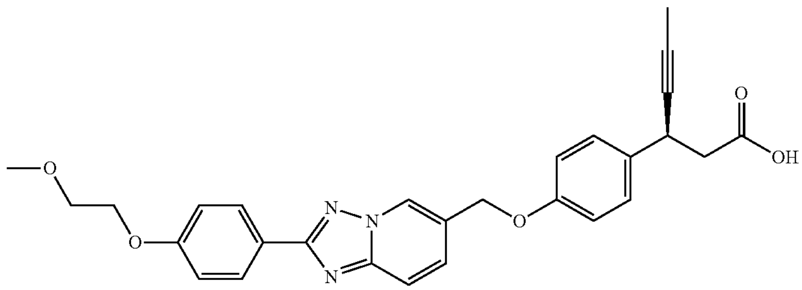 [SMILES: CC#C[C@@H](CC(=O)O)c1ccc(OCc2ccc3nc(-c4ccc(OCCOC)cc4)nn3c2)cc1] | 486 |
| 4[a] | (3S)-3-[4-[[2-[4-(Propan-2-yl)phenyl][1,2,4]triazolo[1,5-a]pyridin-6-yl]methoxy]phenyl]hex-4-ynoic acid | 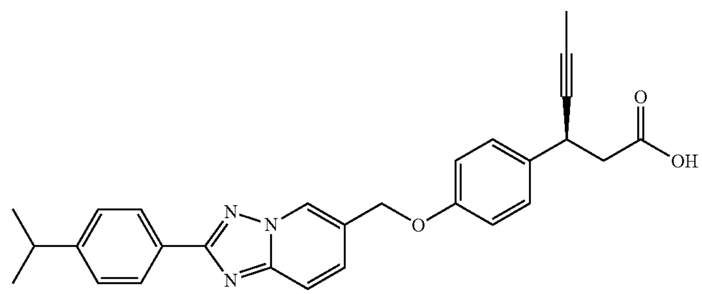 [SMILES: CC#C[C@@H](CC(=O)O)c1ccc(OCc2ccc3nc(-c4ccc(C(C)C)cc4)nn3c2)cc1] | 454 |
| 5[b] | (3S)-3-[4-[[2-[4-(3-Hydroxy-3-methyl-butoxy)phenyl][1,2,4]triazolo[1,5-a]pyridin-6-yl]methoxy]-phenyl]hex-4-ynoic acid | 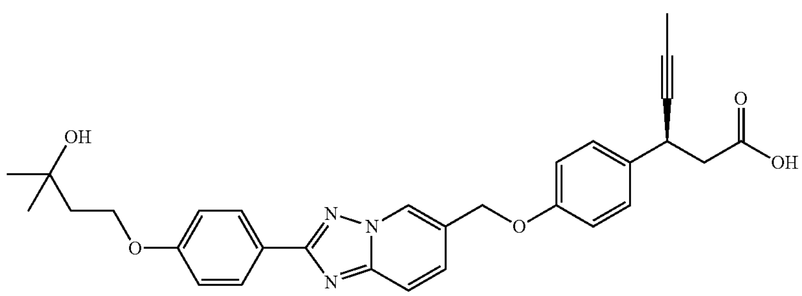 [SMILES: CC#C[C@@H](CC(=O)O)c1ccc(OCc2ccc3nc(-c4ccc(OCCC(C)(C)O)cc4)nn3c2)cc1] | 514 |

[a]5N NaOH is added at 0° C.
[b]Reaction is completed in methanol.

EXAMPLE 6

(3S)-3-[4-[[2-[2,6-Dimethyl-4-[3-(methylsulfonyl)propoxy]phenyl][1,2,4]triazolo[1,5-a]pyridin-6-yl]methoxy]phenyl]hex-4-ynoic acid

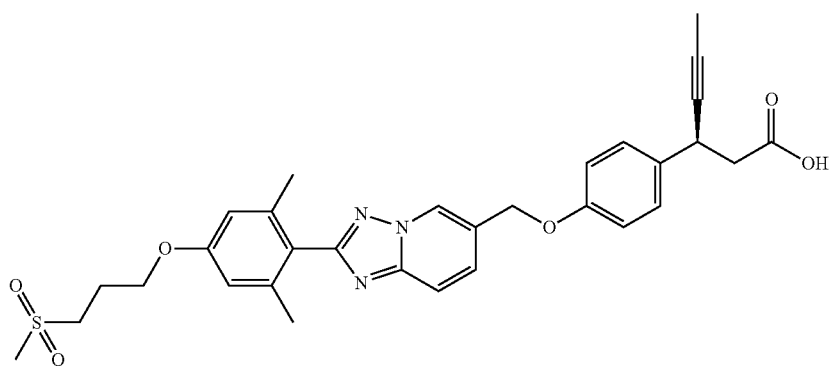 [SMILES: CC#C[C@@H](CC(=O)O)c1ccc(OCc2ccc3nc(-c4c(C)cc(OCCCS(C)(=O)=O)cc4C)nn3c2)cc1]

To a solution of (S)-3-(4-{2-[4-(3-methanesulfonyl-propoxy)-2,6-dimethyl-phenyl]-[1,2,4]triazolo[1,5-a]pyridin-6-ylmethoxy}-phenyl)-hex-4-ynoic acid ethyl ester (0.145 g, 0.238 mmol) in EtOH (5 mL) is added 5 N NaOH solution (0.14 mL, 0.715 mmol) at room temperature and the reaction mixture is heated at 50° C. for 30 minutes. The reaction mixture is evaporated and the residue is dissolved in water (5 mL), washed with ether (2×5 mL), and acidified with aqueous citric acid solution (pH-6) at 0° C. The precipitate solid is filtered and dried to give the title compound as an off-white solid (0.075 g, 55%). LCMS m/z 576 [M+H]⁺.

EXAMPLE 7

(S)-3-{4-[2-(4-Cyano-phenyl)-[1,2,4]triazolo[1,5-a]pyridin-6-ylmethoxy]-phenyl}-hex-4-ynoic acid

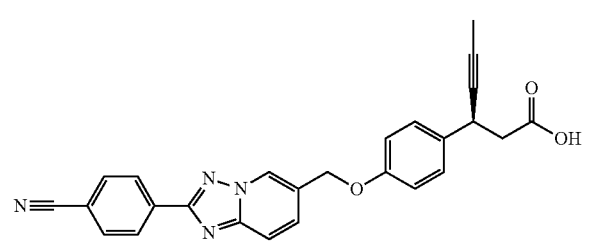 [SMILES: CC#C[C@@H](CC(=O)O)c1ccc(OCc2ccc3nc(-c4ccc(C#N)cc4)nn3c2)cc1]

To a solution of (S)-3-{4-[2-(4-cyano-phenyl)-[1,2,4]triazolo[1,5-a]pyridin-6-ylmethoxy]-phenyl}-hex-4-ynoic acid ethyl ester (0.130 g, 0.2795 mmol) in THF (10 mL) is added potassium trimethylsilanoate (0.143 g, 1.118 mmol) and the reaction mixture is stirred at room temperature for 2 hours. The reaction mixture is evaporated to dryness, the residue is washed with n-pentane, redissolved in water (5 mL) and is acidified with saturated citric acid solution (pH ~5). The precipitated solid is filtered, washed with water, and dried to give the title compound as an off-white solid (0.113 g, 56.5%). LCMS m/z 437 (M+H)⁺.

EXAMPLE 8

(3S)-3-[4-[[2-(4-Difluoromethoxy)phenyl]-[1,2,4]triazolo[1,5-a]pyridin-6-yl]methoxy]phenyl]hex-4-ynoic acid

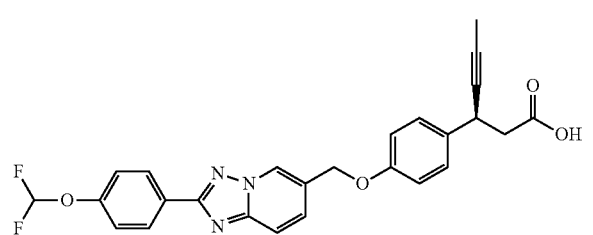 [SMILES: CC#C[C@@H](CC(=O)O)c1ccc(OCc2ccc3nc(-c4ccc(OC(F)F)cc4)nn3c2)cc1]

To a solution of (S)-3-{4-[2-(4-difluoromethoxy-phenyl)-[1,2,4]triazolo[1,5-a]pyridin-6-ylmethoxy]-phenyl}-hex-4-ynoic acid ethyl ester (0.15 g, 0.29 mmol) in THF (8 mL) and water (2 mL) is added 3 N LiOH.H₂O (0.1 mL, 0.89 mmol) and the reaction mixture is stirred at room temperature for 48 hours. The reaction mixture is evaporated to dryness, the residue is washed with n-pentane, redissolved in water (5 mL) and is acidified with saturated citric acid solution (pH ~5). The precipitated solid is filtered, washed with water, and dried to give the title compound as an off-white solid (0.83 g, 59.2%). LCMS m/z 478 (M+H)⁺.

GPR-40

Information

Results of studies using transgenic mice over-expressing the human GPR-40 gene under control of the insulin II promoter recently reported by Nagasumi further support that GPR-40 plays an important role in the regulation of GDIS and plasma glucose levels in-vivo, especially in rodent models of insulin resistance. Nagasumi K, et. al., *Overexpression of GPR-40 in pancreatic β-cells augments glucose-stimulated insulin secretion and improves glucose tolerance in normal and diabetic mice*, Diabetes 58: 1067-1076, 2009. See also, Briscoe C P et al., *The orphan G protein-coupled receptor GPR-40 is activated by medium and long chain fatty acids*, Journal Biological Chemistry 278: 11303-11311, 2003. These findings further support that the development of new GPR-40 modulator compounds may be particularly desired for use in the treatment of T2D.

Assays

Calcium Flux Primary Assays

These assays are used to screen compounds by measuring the increase in intracellular calcium levels that results when a ligand binds and activates GPR-40, thus demonstrating the potency and efficacy of GPR-40 agonists. HEK293 cells over expressing the human GPR-40 cDNA maintained in Dulbecco's modified Eagle's medium with F12 medium in 3:1 ratio supplemented with 10% FBS and 800 µg/ml geneticin at 37° C. and 5% $CO_2$ are employed for the study. Agonist assays are performed using a Calcium 4 Dye assay kit (Molecular Devices) in the presence or absence of 0.1% fatty acid free BSA in the assay buffer (1×HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine the agonist response. The $EC_{50}$ value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 119 nM (±27.4, n=7) and 76% efficacy (±0.8, n=5) when examined in this assay. These results further demonstrate the desired potency and efficacy of Example 1 as a GPR-40 agonist. (Mean±SEM; SEM=standard error of the mean.)

The compounds exemplified herein are tested essentially as described above and exhibit an $EC_{50}$ value for the Calcium Flux Primary assay of lower than 500 nM and >35% efficacy. These results for the exemplified compounds demonstrate the desired potency and efficacy for a GPR-40 agonist.

Selectivity Assays

Peroxisome Proliferator-Activated Receptor (PPAR) α, δ, and γ Functional Assays

Because GPR-40 is known to be activated by ligands to PPARγ, exemplified compounds are examined in PPARα, PPARδ, and PPARγ reporter assays to determine the selectivity of an exemplified compound. CV1 cells, which are derived from the renal tissue of an African green monkey, are transfected with various receptor and reporter plasmids using Fugene. For the PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding domain. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 cm² cell culture flasks in DMEM media with 5% charcoal-stripped FBS and the specific plasmids for the individual assay. After an overnight incubation, transfected cells are trypsinized, plated in opaque 96 well dishes (15,000 cells/well) in DMEM media containing 5% charcoal-stripped FBS, incubated for 4 hours, and exposed to 0.17 ηM to 10 μM of test compound or reference compound in half log dilutions. After 24 hours incubation with compound, cells are lysed and luciferase activity is determined as a measure of receptor activation by luminescence. Data are fitted to a four parameter-fit logistics model to determine $EC_{50}$ values. The maximum percent stimulation is determined versus maximum stimulation obtained with 10 μM of an appropriate PPAR agonist reference compound. Efficacy of <20% is considered negative. No functional activation of PPARα and PPARδ is detected with the compound of Example 1 when examined up to 10 μM in the specific PPAR co-transfection (CTF)/functional assays described above. The $EC_{50}$ for the compound of Example 1 in the PPARγ CTF assay is 2.6 μM. Because the % efficacy in this assay with compound of Example 1 is 17%, the compound is considered negative for PPARγ activity. Thus, the assays support that the Example 1 compound avoids PPAR agonist activity, as desired.

In Vitro Binding Affinity to GPR-40

Radioligand competition binding assays using rapid-wash filtration with a custom prepared radiolabel (5 nM [³H] (TAK-875)) and membranes prepared from HEK293 cells overexpressing the human GPR-40 (hGPR-40) construct are run to determine equilibrium dissociation constants ($K_i$) for an exemplified compound. Competition curves are plotted as the percent specific inhibition versus concentration of compound and analyzed using a four parameter nonlinear regression fit with variable slope. $K_i$ values are calculated using the Cheng-Prusoff equation=$IC_{50}/(1+(D/K_d))$, where $IC_{50}$ is the concentration of compound resulting in 50% inhibition of binding, D is the concentration of radioligand used in the assay and $K_d$ is the equilibrium dissociation constant for the receptor and the radioligand, determined from saturation binding analysis experiments ($K_d$ for [³H] TAK-875=6.2). See Cheng, Y. and Prusoff, W. H. (1973) "Relationship between the inhibition constant ($K_i$) and the concentration of inhibitor which causes 50 per cent inhibition ($IC_{50}$) of an enzymatic reaction," *Biochem Pharmacol* 22(23):3099-3108. For Example 1, $K_i$=14.9 nM±3.5, n=4. (Mean±SEM; SEM=standard error of the mean.). These data demonstrate that Example 1 compound is a ligand for human GPR-40.

Competition Binding Kinetics

Determination of Receptor Residence Time

The association and dissociation rates of unlabeled compound are quantified using the method described by Motulsky, H. J. and L. C. Mahan (1984), "The kinetics of competitive radioligand binding predicted by the law of mass action" *Mol Pharm* 25(1): 1-9. Human GPR-40 membranes are incubated at various time points with 6-8 nM [³H] of a GPR-40 agonist standard (TAK-875) in the absence or presence of $1×K_i$, $3×K_i$, or $10×K_i$ unlabeled exemplified compound. Separation of bound and free radioligand is performed using rapid-wash filtration onto glass fiber filters and counted in a liquid scintillation counter. Rates are calculated by fitting the data to the kinetics of competitive binding model in GraphPad Prism 6, version 6.03 for Windows, GraphPad Software, La Jolla Calif. USA. Example 1 shows a GPR-40 residence time, τ, to be 30.2 min (±3.2, n=3), which suggests that this GPR-40 ligand has residence time on the receptor associated with an in-vivo response. (Mean+SEM; SEM=standard error of the mean.)

Human and Mouse Beta-Arrestin Agonist Assay with 1% FBS to Determine Beta-Arrestin Recruitment Human embryonic kidney (hEK293)-hFFAR1 cells are purchased from DiscoveRx™. Human osteosarcoma (U2OS) cells expressing mFFAR1 are developed by DiscoveRX™. These cells co-express the Prolink™ (PK)-tagged GPR-40 and the Enzyme Acceptor™ (EA)-tagged beta-arrestin fusion proteins. If activation of the GPR-40 stimulates beta-arrestin recruitment, it would force complementation of the beta galactosidase (B-gal) enzyme fragments, forming a B-gal enzyme that generates a chemiluminescent signal using the DiscoveRx PathHunter™ detection kit. Cells are incubated overnight at 5,000 cells/well in 384 well plates in culture media containing 1% FBS (fetal bovine serum). Serial diluted compound in DMSO (2× dilutions to generate 20 concentrations) are step down diluted in culture media containing 1% FBS (fetal bovine serum) and added to cells with a final top concentration starting of 100 μM. After addition of compound, cells are incubated for 90 min at 37° C. in 5% $CO_2$ incubator, and DiscoveRX™ kit detection reagents are added. Measurement of the chemiluminescent signal is ascertained with the Envision™ reader, after a 1-hour incubation at room temperature. Data are fit to a 4 parameter-fit logistics to determine $EC_{50}$ values, % activity is measured versus maximum response to an internal standard GPR-40 agonist at 1 μM. For hGPR-40 b-arrestin, Example 1, has an $EC_{50}$ of 44.8 nM (±17.9, n=4) with a % stimulation max (FA) of 128 (±10.9, n=4) and mGPR-40 b-arrestin of 3.63 nM (±0.81, n=7) with a % stimulation max (FA) of 153 (+5.64, n=7). (Mean+SEM; SEM=standard error of the mean.) These data indicate that the compound of Example 1 can signal through the beta arrestin pathway.

Chronic Oral Glucose Tolerance Test (OGTT) in Zucker Fa/Fa Rats

OGTTs are performed in Zucker fa/fa rats, a rodent model of insulin resistance, after 1 and 21 days of orally administered exemplified compound at 1.0, 3.0 and 10 mg/kg. A standard GPR-40 agonist at 1 mg/kg serves as the positive control. OGTTs are performed one hour post compound administration with blood samples taken for determination of glucose and insulin levels at 10, 20, 40, 60, and 120 minutes post glucose administration. On days 1 and 21, the AUCs for glucose lowering are statistically significant (p<0.05) for all doses of compound of Example 1 tested (1, 3, and 10 mg/kg) and with the positive control. Insulin AUCs demonstrate a dose dependent elevation during the OGTTs; although, these values are not statistically significant. Weight and food consumption are not altered due to any treatment during the study. The ED$_{90}$ for glucose lowering using a compound of Example 1 on day 1 is 4.1 mg/kg and on day 21 is 5.0 mg/kg. These findings suggest that GPR-40 is not desensitized following 21 days of oral administration with a compound of Example 1.

In Vivo Efficacy

Intraperitoneal Glucose Tolerance Test (IPGTT)

To examine the ability of the compound of Example 1 to activate GPR-40 in-vivo resulting in anti-diabetic efficacy, i.e. reduction in plasma glucose levels, an intraperitoneal glucose tolerance test (ipGTT) study is completed, and the data is shown for the compound of Example 1, below in Table 7.

Male Balb/c (Albino mice) mice (8-9 weeks of age) are single housed, and fed with normal rodent chow diet and water ad libitum. Animals are weighed; randomized by body weight; and their daily body weights are recorded. On the night before the study, animals are fasted overnight. In the morning, animals are dosed orally with compound of Example 1 or vehicle alone 60 minutes prior to the glucose tolerance test (glucose 2 g/kg, i.p.). Blood glucose levels are determined from tail bleeds taken at 0, 3, 7, 15, 30, and 60 min after glucose challenge. The blood glucose excursion profile from t=0 to t=60 min is used to integrate an area under the curve (AUC) for each treatment. Percent lowering in glucose is calculated from the AUC data of the compound with respect to the AUC of vehicle group. The compound of Example 1 is orally administered at 0.1, 0.3, 1.0, 3.0, 10, or 30 mg/kg, and a positive control (3-[4-(2-methyl-benzyloxy)-phenyl]-hex-4-ynoic acid) is administered at 10 mg/kg. No concentration of compound of Example 1 or the positive control significantly lowered glucose levels at the 3 or 7 minute time points during the GTT. Glucose levels were significantly lowered with the 30 mg/kg dose of compound of Example 1 at the 15 minute time point; with the 1.0, 10 and 30 mg/kg doses and the positive control at the 30 minute time point; and with the 3.0, 10 and 30 mg/kg doses plus the positive control at the 60 minute time point. The ED$_{50}$ for the compound of Example 1 based on AUCs for glucose lowering is 7.6 mg/kg. Results from this study demonstrate that activation of GPR-40 by Example 1 leads to in-vivo anti-diabetic efficacy.

Effect on Blood Glucose, Statistical Significance for Various Treatment Groups as Compared to Vehicle During ipGTT

TABLE 7

| Treatment | Dose (mpk) | Time | | | | | |
|---|---|---|---|---|---|---|---|
| | | 0 | 3 | 7 | 15 | 30 | 60 |
| control (TAK875) | 10 | Ns | ns | ns | Ns | **** | **** |
| Example 1 | 0.1 | Ns | ns | ns | Ns | ns | ns |
| | 0.3 | Ns | ns | ns | ns | ns | ns |
| | 1 | Ns | ns | ns | ns | * | ns |
| | 3 | Ns | ns | ns | ns | ns | ** |
| | 10 | Ns | ns | ns | ns | **** | **** |
| | 30 | Ns | ns | ns | ** | **** | **** |

*P < 0.05,
**P < 0.01,
****P < 0.0001
Two way anova followed by Bonferroni post test, ns: not significant The exemplified compounds of the present invention can be readily formulated into pharmaceutical compositions in accordance with accepted practices known in the art such as found in Remington's "Pharmaceutical Sciences", Gennaro, Ed., Mack Publishing Co. Easton Pa. 1990 such as tablets, solid or gel filled capsules, powders, suspensions, or solutions. The composition can also include one or more pharmaceutically acceptable carriers, excipients, and diluents.

Preferred pharmaceutical compositions are formulated as a tablet or capsule for oral administration. The tablet or capsule can include a compound of the present invention in an amount effective to treat diabetes particularly type two diabetes.

The pharmaceutical composition is administered to a patient in amounts effective to treat diabetes, more particularly, type two diabetes. An appropriate amount or dose effective to treat a patient can be determined by a health care provider.

What is claimed is:
1. A compound of the Formula

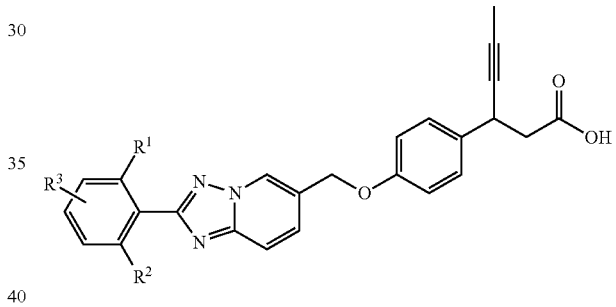

wherein
R$^1$ is selected from the group consisting of H and CH$_3$;
R$^2$ is selected from the group consisting of H and CH$_3$;
R$^3$ is selected from the group consisting of H, C$_1$-C$_3$ alkyl, O(CH$_2$)$_3$SO$_2$CH$_3$, O(CH$_2$)$_2$OCH$_3$, O(CH$_2$)$_2$C(CH$_3$)$_2$OH, CN, and OCF$_2$;
or a pharmaceutically acceptable salt thereof.

2. A compound as claimed by claim 1 wherein the compound is

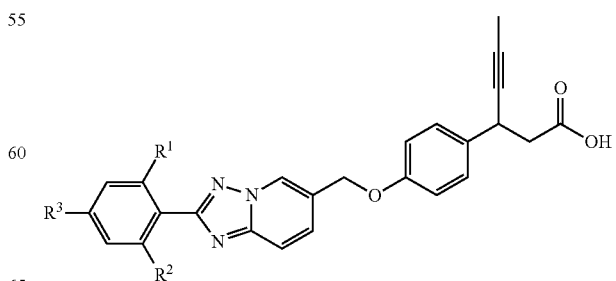

or a pharmaceutically acceptable salt thereof.

3. A compound as claimed by claim 2 wherein $R^3$ is selected from the group consisting of $C_1$-$C_3$ alkyl, $O(CH_2)_3SO_2CH_3$, $O(CH_2)_2OCH_3$, $O(CH_2)_2C(CH_3)_2OH$, CN, and $OCF_2$.

4. A compound as claimed by claim 3 wherein $R^1$ is H.

5. A compound as claimed by claim 1 wherein $R^2$ is H.

6. A compound as claimed by claim 1 wherein $R^2$ is $CH_3$.

7. A compound as claimed by claim 1 where in the compound is:

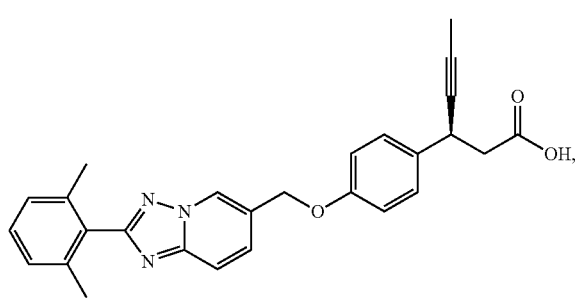 [SMILES: CC#C[C@@H](CC(=O)O)c1ccc(OCc2ccc3nc(-c4c(C)cccc4C)nn3c2)cc1]

or a pharmaceutically acceptable salt thereof.

8. A compound as claimed by claim 7 wherein the compound is (3S)-3-[4-[[2-(2,6-Dimethylphenyl)-[1,2,4]triazolo[1,5-a]pyridin-6-yl]methoxy]phenyl]hex-4-ynoic acid.

9. A pharmaceutical composition comprising a compound as claimed by claim 1 or a pharmaceutically acceptable salt thereof and at least one of a pharmaceutically acceptable carrier, diluent, or excipient.

10. A method of treating diabetes in a mammal in need thereof, comprising administering an effective amount of a compound as claimed by claim 1, or a pharmaceutically acceptable salt thereof.

11. An intermediate compound of the formula

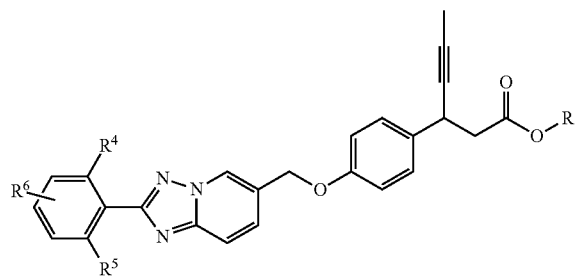

wherein
  R is selected from the group consisting of $C_{1-4}$ alkyl, $C_{1-4}$ haloalkyl, $C_{3-6}$ cycloalkyl, —$C_{1-4}$ alkyl-$C_{3-6}$ cycloalkyl, phenyl, and $C_{1-5}$ alkylphenyl;
  $R^4$ is selected from the group consisting of H and $CH_3$;
  $R^5$ is selected from the group consisting of H and $CH_3$; and
  $R^6$ is selected from the group consisting of H, $C_1$-$C_3$ alkyl, $O(CH_2)_3SO_2CH_3$, $O(CH_2)_2OCH_3$, $O(CH_2)_2C(CH_3)_2OH$, CN, and $OCF_2$;
  or a pharmaceutically acceptable salt thereof.

12. An intermediate compound as claimed by claim 11 wherein the compound is

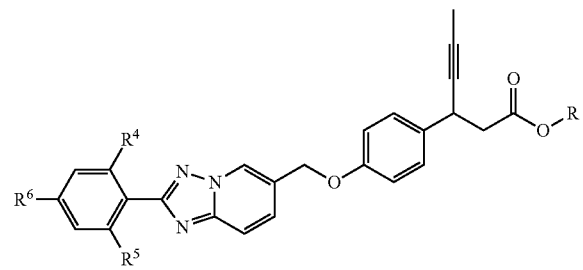

or a pharmaceutically acceptable salt thereof.

13. An intermediate compound as claimed by claim 12 wherein R is selected from the group consisting of $C_{1-4}$ alkyl, phenyl, and benzyl.

14. An intermediate compound as claimed by claim 13 wherein R is selected from the group consisting of methyl and ethyl.

15. An intermediate compound as claimed by claim 11 wherein the compound is

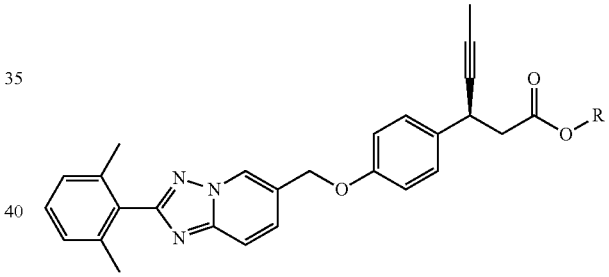

or a pharmaceutically acceptable salt thereof.

16. A process for preparing (3S)-3-[4-[[2-(2,6-Dimethylphenyl)-[1,2,4]triazolo[1,5-a]pyridin-6-yl]methoxy]phenyl]hex-4-ynoic acid or a pharmaceutically acceptable salt thereof, comprising de-esterifying an intermediate compound of the Formula;

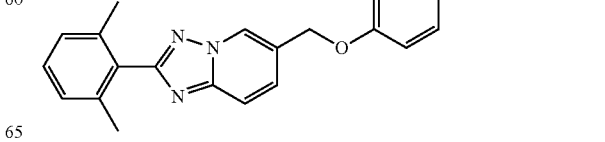

to provide a compound of the Formula,
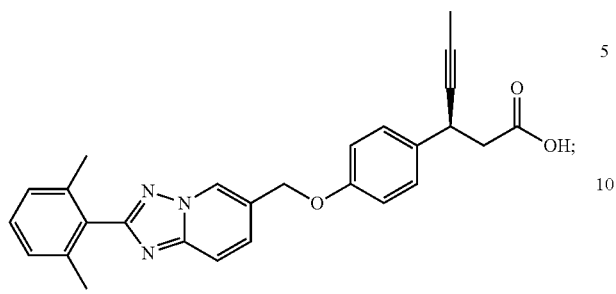
or a pharmaceutically acceptable salt thereof.
* * * * *